(12) United States Patent
Leung et al.

(10) Patent No.: US 6,254,868 B1
(45) Date of Patent: Jul. 3, 2001

(54) GLYCOSYLATED HUMANIZED B-CELL SPECIFIC ANTIBODIES

(75) Inventors: Shui-on Leung, Madison; Hans Hansen, Mystic Island; Zhengxing Qu, Warren, all of NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 09/155,107

(22) PCT Filed: Mar. 19, 1997

(86) PCT No.: PCT/US97/04196

§ 371 Date: Nov. 17, 1998

§ 102(e) Date: Nov. 17, 1998

(87) PCT Pub. No.: WO97/34632

PCT Pub. Date: Sep. 25, 1997

Related U.S. Application Data

(60) Provisional application No. 60/013,709, filed on Mar. 20, 1996.

(51) Int. Cl.$^7$ ............................................. A61K 39/395
(52) U.S. Cl. ........................... 424/178.1; 424/130.1; 424/133.1; 424/155.1; 530/387.3; 530/388.85; 530/391.3; 530/391.7
(58) Field of Search ............................ 530/391.7, 387.1, 530/387.3, 388.1, 388.85, 391.3, 388.8; 536/23.1, 23.5, 23.53; 424/155.1, 133.1, 156.1; 435/69.6

(56) References Cited

U.S. PATENT DOCUMENTS 4,474,893 * 10/1984 Reading et al. .
4,722,899 * 2/1988 Hamaoka et al. .
5,057,313   10/1991 Shih et al. .
5,635,603 *  6/1997 Hansen et al. .
5,789,554    8/1998 Leung et al. .

FOREIGN PATENT DOCUMENTS 0 239 400   9/1987 (EP) .

OTHER PUBLICATIONS

Dalente, Trends in Biotechnology 3:9, 1985.*
Seaver, Genetic Engineering News 14, pp. 10 and 21, 1994.*
Sevier et al., Clin. Chem. 27:1797–06, 1981.*
Panka et al., Proc. Natl. Acad. Sci. USA 85:3080–3084, 1988.*
Amit et al., Science 233:747–53, 1986.*
Wright et al., Springer Semin. Immunopath. 15:259–273, 1993.*
Tao et al., J. of Immunol. 143:2595–2601, 1989.*
Rudikoff et al., Proc. Natl. Acad. Sci. USA 79:1979–83, 1982.*
Lazar et al., Mol. and Cell. Biol. 8:1247–1252, 1988.*
Burgess et al., J. of Cell. Biol. 111:2129–2138, 1990.*
Olden et al., BBA 650:209–232, 1982.*
Lewin, Genes IV, p. 810, 1990.*
Skerra et al., FEBS Letters 271:203–206, 1990.*
Gussow et al., Meth. in Enz. 203:99–121. 1991.
Morrison, et al., Proc. Nat. Acad. Sci. USA 81:6851–6855. 1984.
Belise et al., Proc. of the Am. Assn. for Can. Res., vol. 34, p. 481, #2873 (Mar. 1993).
Mills, G., Proc. of the Am. Assn. for Can. Res., vol. 34, p. 479 (Mar. 1993).
Goldenberg, D., Scientific Am. Sci. & Med., pp. 64–73, (Mar./Apr. 1994).
Thorpe, R, TIBTECH, vol. 11, pp. 40–42 (Feb. 1993).
Queen et al., PNAS 86:10029–10033 (1989).
Baum, et al, Cancer 73 (3 Supl): 896–899 (Feb. 1, 1994).
Riechmann, et al, Nature 332: 323–327 (1988).
Kreitman, et al., Cancer Research, 53:819–825 (Feb. 15, 1993).
Shih, et al., Int. J. Cancer, 56:538–545 (1994).
Goldenberg, D., J. Clin. Oncology, 9(4):548–564 (Apr. 1991).
Jost, et al., J. of Biological Chemistry, 269(42):26267–26273:(Oct. 21, 1994).
Wallick, et al., J. Exp. Med., 168:1099–1109 (Sep. 1988).
Olender, et al., J. of Biological Chemistry, 267(6):4223–4235 (Feb. 25, 1992).
Leung, et al., J. of Immunology, 154:5919–5926 (Jun. 1, 1995).

* cited by examiner

Primary Examiner—Sheela Huff
Assistant Examiner—Larry R. Helms
(74) Attorney, Agent, or Firm—Foley & Lardner

(57) ABSTRACT

A humanized specific monoclonal antibody or antibody fragment, especially a B-cell specific antibody or antibody fragment, is engineered to contain a glyxosylation site in the non-Fc constant region. The glycosylated antibody is useful for diagnosis and/or therapy whenever a targeting antibody or fragment is used, especially for B-cell malignancies. The carbohydrate moiety allows conjugation of labeling or therapeutic agents of increased size, without affecting the binding affinity or specificity of the antibody.

12 Claims, 16 Drawing Sheets

FIG. 1A

```
                           *            **
murine LL2   DIQLTQSPSSLAVSAGENVTMSC KSSQSVLYSANHKNYLA WYQQKPGQSPKLLIY
LL2 REIHuVK  ---------SA-V-DR------ ----------------  ----------KA---
REI FRs      DIQMTQSPSSLSASVGDRVTITC                  WYQQTPGKAPKLLIY L2
                                                      WASTRES
                                                      -------

L3
                                   *
murine LL2   GVPDRFTGSGSGTDFTLTISRVQVEDLAIYYC HQYLSSWT
LL2 REIHuVK  ---S--S-------F---SL-P---I-T---  --------
REI FRs      GVPSRFSGSGSGTDYTFTISSLQPEDIATYYC

*  *
             FGGGTKLEIKR
             -----------
             FGQGTKLQITR
```

FIG. 1B

```
                                                    ★  ★                      ★
                  FR1                                           H1           FR2
MURINE      QVQLQESGAELSKPGASVKMSCKASGYTFT         SYWLH      WIKQRPGQGLEWIG
EUHuVH1     ----Q-------------VK---S--V-          -----      ------VR-A----
EUHuVH2     -----VQ-----------VK---S--V-          -----      ------VR-A----

★★                                    ★
                     H2                              FR3
MURINE        YINPRNDYTEYNQNFKD        KATLTADKSSSTAYMQLSSLTSEDSAVYYCAR
EUHuVH1       ----------------         -I--E-TN-------R-------T-F-F--
EUHuVH2       ----------------         -I--E-TN-------R-------T-F-F--

H3              FR4
MURINE       RDITTFY           WGQGTTLTVSS
NEWMHuVH1    -------           -------V---
NEWMHuVH2    -------           -------V---
```

```
         GACATTCAGCTGACCCAGTCTCCATCATCTCTGGCTGTGTCTGCAGGAGAAAACGTCACT
  1  ----+----+----+----+----+----+  60
         CTGTAAGTCGACTGGGTCAGAGGTAGTAGAGACCGACAGACGTCCTCTTTTTGCAGTGA
         D   I   Q   L   T   Q   S   P   S   S   L   A   V   S   A   G   E   N   V   T  -
                                                                                    ___

ATGAGCTGTAAGTCCAGTCAGAGTGTTTTATACAGTGCAAATCACAAGAACTACTTGGCC
 61  ----+----+----+----+----+----+  120
         TACTCGACATTCAGGTCAGTCTCACAAAATATGTCACGTTTAGTGTTCTTGATGAACCGG
         M   S   C  |K   S   S   Q   S   V   L   Y   S   A   N   H   K   N   Y   L   A| -
                                            CDR1

TGGTACCAGCAGAAACCAGGACAGTCTCCTAAACTGCTGATCTACTGGGCATCCACTAGG
121  ----+----+----+----+----+----+  180
         ACCATGGTCGTCTTTGGTCCTGTCAGAGGATTTGACGACTAGATGACCCGTAGGTGATCC
         W   Y   Q   Q   K   P   G   Q   S   P   K   L   L   I   Y  |W   A   S   T   R| -
                                                                         CDR2

GAATCTGGTGTGTCCCTGATCGCTTCACAGGCGGATCTGGGACAGAGATTTTACTCTTACC
181  ----+----+----+----+----+----+  240
         CTTAGACCACACAGGGACTAGCGAAGTGTCCGTCCGCCTAGACCCTGTCTCTAAAATGAGAATGG
         |E   S| G   V   P   D   R   F   T   G   S   G   S   G   T   D   F   T   L   T  -

ATCAGCAGAGTACAAGTTGAAGACCTGGCAATTTATTATTGTCACCAATACCTCTCCTCG
241  ----+----+----+----+----+----+  300
         TAGTCGTCTCATGTTCAACTTCTGGACCGTTAAATAATAACAGTGGTTATGGAGAGGAGC
         I   S   R   V   Q   V   E   D   L   A   I   Y   Y   C  |H   Q   Y   L   S   S| -
                                                                         CDR3

TGGACGTTCGGTGGAGGGACCAAGCTGGAGATCAAACGT
301  ----+----+----+--- 339
         ACCTGCAAGCCACCTCCCCTGGTTCGACCTCTAGTTTGCA
         |W| T   F   G   G   G   T   K   L   E   I   K   R  -
```

```
     CAGGTCCAGCTGCAGGAGTCAGGGGCTGAACTGTCAAAACCTGGGGCCTCAGTGAAGATG
1    ------------+----------+----------+----------+----------+----------+ 60
     GTCCAGGTCGACGTCCTCAGTCCCCGACTTGACAGTTTTGGACCCCGGAGTCACTTCTAC

Q   V   Q   L   Q   E   S   G   A   E   L   S   K   P   G   A   S   V   K   M  -

TCCTGCAAGGCTTCTGGCTACACCTTTACTAGCTACTGGCTGCACTGGATAAAACAGAGG
61   ------------+----------+----------+----------+----------+----------+ 120
     AGGACGTTCCGAAGACCGATGTGGAAATGATCGATGACCGACGTGACCTATTTTGTCTCC
                                         CDR1
      S   C   K   A   S   G   Y   T   F   T  |S   Y   W   L   H|  W   I   K   Q   R  -

CCTGGACAGGGTCTGGAATGGATTGGATACATTAATCCTAGGAATGATTATACTGAGTAC
121  ------------+----------+----------+----------+----------+----------+ 180
     GGACCTGTCCCAGACCTTACCTAACCTATGTAATTAGGATCCTTACTAATATGACTCATG
                                    CDR2
      P   G   Q   G   L   E   W   I   G  |Y   I   N   P   R   N   D   Y   T   E   Y| -

AATCAGAACTTCAAGGACAAGGCCACATTGACTGCAGACAAATCCTCCAGCACAGCCTAC
181  ------------+----------+----------+----------+----------+----------+ 240
     TTAGTCTTGAAGTTCCTGTTCCGGTGTAACTGACGTCTGTTTAGGAGGTCGTGTCGGATG

|N   Q   N   F   K   D|  K   A   T   L   T   A   D   K   S   S   S   T   A   Y  -

ATGCAACTGAGCAGCCTGACATCTGAGGACTCTGCAGTCTATTACTGTGCAAGAAGGGAT
241  ------------+----------+----------+----------+----------+----------+ 300
     TACGTTGACTCGTCGGACTGTAGACTCCTGAGACGTCAGATAATGACACGTTCTTCCCTA

M   Q   L   S   S   L   T   S   E   D   S   A   V   Y   Y   C   A   R  |R   D| -

ATTACTACGTTCTACTGGGGCCAAGGCACCACTCTCACAGTCTCCTCG
301  ------------+----------+----------+----------+------ 348
     TAATGATGCAAGATGACCCCGGTTCCGTGGTGAGAGTGTCAGAGGAGC
         CDR3
     |I   T   T   F   Y|  W   G   Q   G   T   T   L   T   V   S   S  -
```

FIG. 5A

```
    GACATTCAGCTGACCCAGTCTCCATCATCTCTGAGCGCATCTGTTGGAGATAGGGTCACT
  1 ------+---------+---------+---------+---------+---------+  60
    CTGTAAGTCGACTGGGTCAGAGGTAGTAGAGACTCGCGTAGACAACCTCTATCCCAGTGA
    D   I   Q   L   T   Q   S   P   S   S   L   S   A   S   V   G   D   R   V   T   -

ATGAGCTGTAAGTCCAGTCAAAGTGTTTTATACAGTGCAAATCACAAGAACTACTTGGCC
 61 ------+---------+---------+---------+---------+---------+ 120
    TACTCGACATTCAGGTCAGTTTCACAAAATATGTCACGTTTAGTGTTCTTGATGAACCGG
    M   S   C  [ K   S   S   Q   S   V   L   Y   S   A   N   H   K   N   Y   L   A ] -
                                       CDR1

TGGTACCAGCAGAAACCAGGGAAAGCACCTAAACTGCTGATCTACTGGGCATCCACTAGG
121 ------+---------+---------+---------+---------+---------+ 180
    ACCATGGTCGTCTTTGGTCCCTTTCGTGGATTTGACGACTAGATGACCCGTAGGTGATCC
    W   Y   Q   Q   K   P   G   K   A   P   K   L   L   I   Y  [ W   A   S   T   R ] -
                                                                        CDR2

GAATCTGGTGTCCCTTCGCGATTCTCTGGCAGCGGATCTGGGACAGATTTTACTTTCACC
181 ------+---------+---------+---------+---------+---------+ 240
    CTTAGACCACAGGGAAGCGCTAAGAGACCGTCGCCTAGACCCTGTCTAAAATGAAAGTGG
   [ E   S ] G   V   P   S   R   F   S   G   S   G   S   G   T   D   F   F   T   -

ATCAGCTCTCTTCAACCAGAAGACATTGCAACGTTCTTCTGTAACGTTGTATAACAGTGGTTATGGAGAGAGC
241 ------+---------+---------+---------+---------+---------+ 300
    TAGTCGAGAGAAGTTGGTCTTCTGTAACGTTGCAAGAAGACATTGCAACATATTATTGTCACCAATACCTCCTCG
    I   S   S   L   Q   P   E   D   I   A   T   Y   Y   C  [ H   Q   Y   L   S   S ] -
                                                                      CDR3

TGGACGTTCGGTGGAGGGACCAAGCTGGAGATCAAACGT
301 ------+---------+---------+--------- 339
    ACCTGCAAGCCACCTCCCTGGTTCGACCTCTAGTTTGCA
   [ W ] T   F   G   G   G   T   K   L   E   I   K   R
```

FIG. 5B

```
    CAGGTCCAGCTGGTCCAATCAGGGGCTGAAGTCAAGAAACCTGGGTCATCAGTGAAGGTC
1   ----------+---------+---------+---------+---------+---------+ 60
    GTCCAGGTCGACCAGGTTAGTCCCCGACTTCAGTTCTTTGGACCCAGTAGTCACTTCCAG

Q   V   Q   L   V   Q   S   G   A   E   V   K   K   P   G   S   S   V   K   V   -

TCCTGCAAGGCTTCTGGCTACACCTTTACTAGCTACTGGCTGCACTGGGTCAGGCAGGCA
61  ----------+---------+---------+---------+---------+---------+ 120
    AGGACGTTCCGAAGACCGATGTGGAAATGATCGATGACCGACGTGACCCAGTCCGTCCGT
                                         CDR1
    S   C   K   A   S   G   Y   T   F   T  |S   Y   W   L   H|  W   V   R   Q   A   -

CCTGGACAGGGTCTGGAATGGATTGGATACATTAATCCTAGGAATGATTATACTGAGTAC
121 ----------+---------+---------+---------+---------+---------+ 180
    GGACCTGTCCCAGACCTTACCTAACCTATGTAATTAGGATCCTTACTAATATGACTCATG
                                         CDR2
    P   G   Q   G   L   E   W   I   G  |Y   I   N   P   R   N   D   Y   T   E   Y| -

AATCAGAACTTCAAGGACAAGGCCACAATAACTGCAGACGAATCCACCAATACAGCCTAC
181 ----------+---------+---------+---------+---------+---------+ 240
    TTAGTCTTGAAGTTCCTGTTCCGGTGTTATTGACGTCTGCTTAGGTGGTTATGTCGGATG

|N   Q   N   F   K   D|  K   A   T   I   T   A   D   E   S   T   N   T   A   Y   -

ATGGAGCTGAGCAGCCTGAGGTCTGAGGACACGGCATTTTATTTTTGTGCAAGAAGGGAT
241 ----------+---------+---------+---------+---------+---------+ 300
    TACCTCGACTCGTCGGACTCCAGACTCCTGTGCCGTAAAATAAAAACACGTTCTTCCCTA

M   E   L   S   S   L   R   S   E   D   T   A   F   Y   F   C   A   R  |R   D| -

ATTACTACGTTCTACTGGGGCCAAGGCACCACGGTCACCGTCTCCTCG
301 ----------+---------+---------+---------+--------- 348
    TAATGATGCAAGATGACCCCGGTTCCGTGGTGCCAGTGGCAGAGGAGC
            CDR3
   |I   T   T   F   Y|  W   G   Q   G   T   T   V   T   V   S   S   -
```

FIG. 6
Designed sequence for humanized LL2 VH domain:
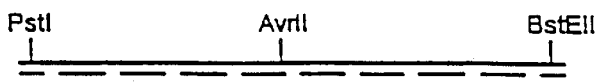
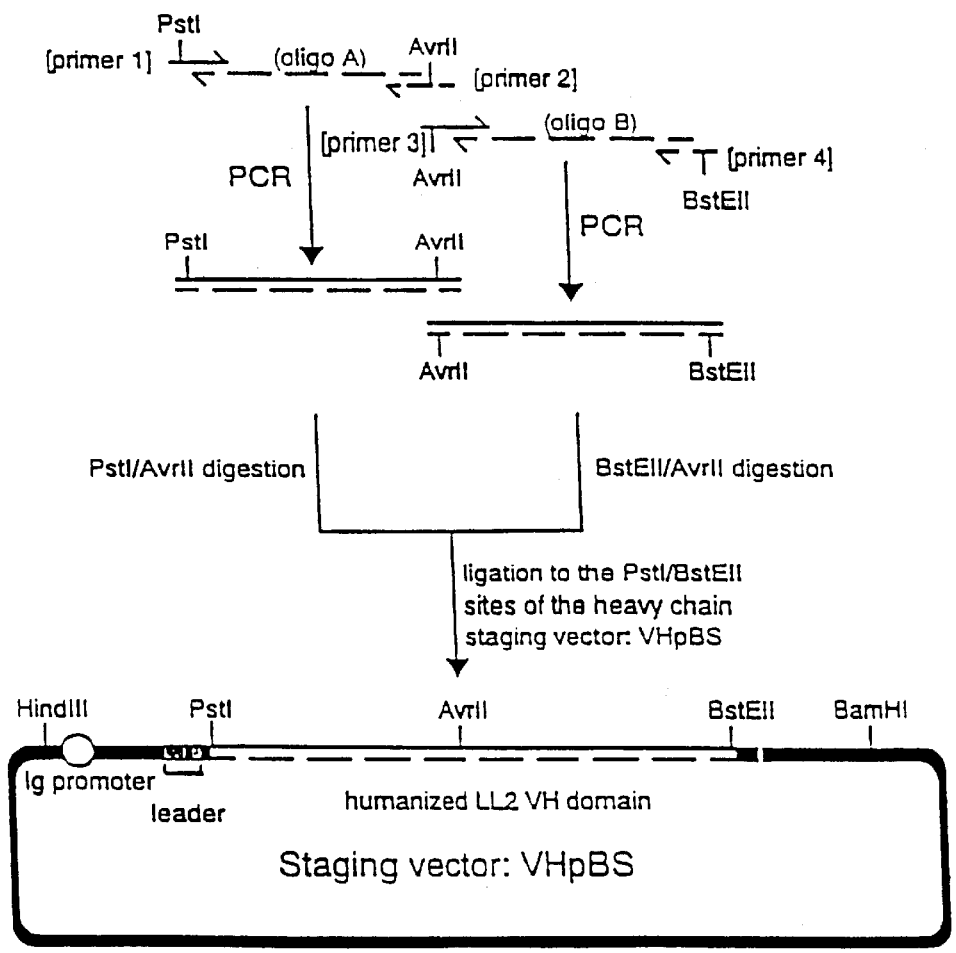

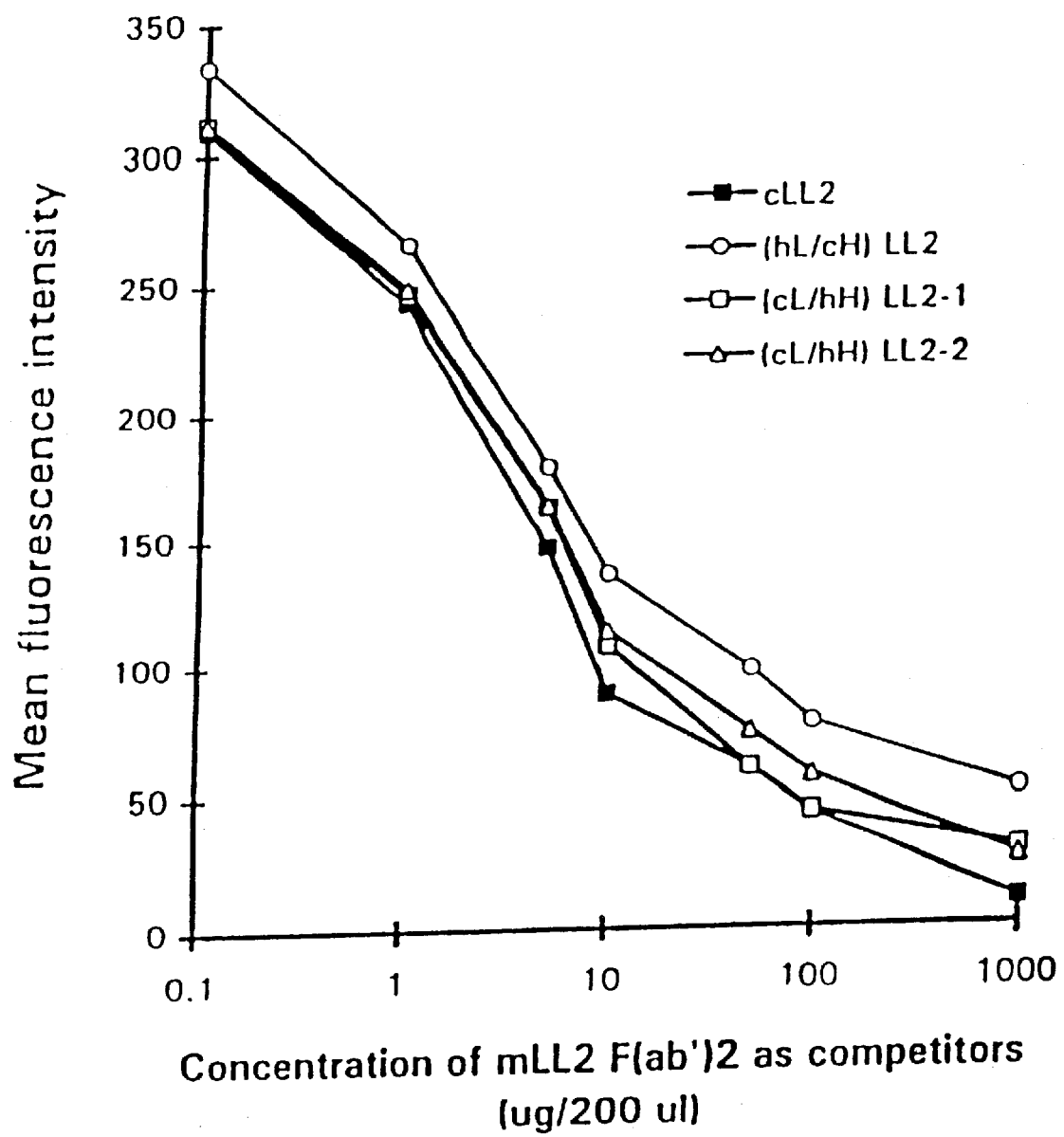

FIG. 12

| β-strand | C | D | E | F |

SEQUENCE LISTING

<160> NUMBER OF SEQ ID NOS: 47

<210> SEQ ID NO 1
<211> LENGTH: 339
<212> TYPE: DNA
<213> ORGANISM: Murine
<220> FEATURE:
<221> NAME/KEY: CDS
<222> LOCATION: (1)..(339)

<400> SEQUENCE: 1

| gac | att | cag | ctg | acc | cag | tct | cca | tca | tct | ctg | gct | gtg | tct | gca | gga | 48 |
| Asp | Ile | Gln | Leu | Thr | Gln | Ser | Pro | Ser | Ser | Leu | Ala | Val | Ser | Ala | Gly | |
| 1 | | | | 5 | | | | | 10 | | | | | 15 | | |

| gaa | aac | gtc | act | atg | agc | tgt | aag | tcc | agt | caa | agt | gtt | tta | tac | agt | 96 |
| Glu | Asn | Val | Thr | Met | Ser | Cys | Lys | Ser | Ser | Gln | Ser | Val | Leu | Tyr | Ser | |
| | | | 20 | | | | | 25 | | | | | 30 | | | |

| gca | aat | cac | aag | aac | tac | ttg | gcc | tgg | tac | cag | cag | aaa | cca | ggg | cag | 144 |
| Ala | Asn | His | Lys | Asn | Tyr | Leu | Ala | Trp | Tyr | Gln | Gln | Lys | Pro | Gly | Gln | |
| | | 35 | | | | | 40 | | | | | 45 | | | | |

| tct | cct | aaa | ctg | ctg | atc | tac | tgg | gca | tcc | act | agg | gaa | tct | ggt | gtc | 192 |
| Ser | Pro | Lys | Leu | Leu | Ile | Tyr | Trp | Ala | Ser | Thr | Arg | Glu | Ser | Gly | Val | |
| | 50 | | | | | 55 | | | | | 60 | | | | | |

| cct | gat | cgc | ttc | aca | ggc | agc | gga | tct | ggg | aca | gat | ttt | act | ctt | acc | 240 |
| Pro | Asp | Arg | Phe | Thr | Gly | Ser | Gly | Ser | Gly | Thr | Asp | Phe | Thr | Leu | Thr | |
| 65 | | | | 70 | | | | | 75 | | | | | 80 | | |

| atc | agc | aga | gta | caa | gtt | gaa | gac | ctg | gca | att | tat | tat | tgt | cac | caa | 288 |
| Ile | Ser | Arg | Val | Gln | Val | Glu | Asp | Leu | Ala | Ile | Tyr | Tyr | Cys | His | Gln | |
| | | | 85 | | | | | 90 | | | | | 95 | | | |

| tac | ctc | tcc | tcg | tgg | acg | ttc | ggt | gga | ggg | acc | aag | ctg | gag | atc | aaa | 336 |
| Tyr | Leu | Ser | Ser | Trp | Thr | Phe | Gly | Gly | Gly | Thr | Lys | Leu | Glu | Ile | Lys | |
| | | | 100 | | | | | 105 | | | | | 110 | | | |

| cgt | | | | | | | | | | | | | | | | 339 |
| Arg | | | | | | | | | | | | | | | | |

<210> SEQ ID NO 2
<211> LENGTH: 113
<212> TYPE: PRT
<213> ORGANISM: Murine

<400> SEQUENCE: 2

Asp Ile Gln Leu Thr Gln Ser Pro Ser Ser Leu Ala Val Ser Ala Gly
 1               5                  10                  15

Glu Asn Val Thr Met Ser Cys Lys Ser Ser Gln Ser Val Leu Tyr Ser
                20                  25                  30

Ala Asn His Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
 65                 70                  75                  80

Ile Ser Arg Val Gln Val Glu Asp Leu Ala Ile Tyr Tyr Cys His Gln
                85                  90                  95

Tyr Leu Ser Ser Trp Thr Phe Gly Gly Gly Thr Lys Leu Glu Ile Lys
                100                 105                 110

Arg

<210> SEQ ID NO 3

```
<211> LENGTH: 348
<212> TYPE: DNA
<213> ORGANISM: Murine
<220> FEATURE:
<221> NAME/KEY: CDS
<222> LOCATION: (1)..(348)

<400> SEQUENCE: 3 cag gtc cag ctg cag gag tca ggg gct gaa ctg tca aaa cct ggg gcc      48
Gln Val Gln Leu Gln Glu Ser Gly Ala Glu Leu Ser Lys Pro Gly Ala
 1               5                  10                  15 tca gtg aag atg tcc tgc aag gct tct ggc tac acc ttt act agc tac      96
Ser Val Lys Met Ser Cys Lys Ala Ser Gly Tyr Thr Phe Thr Ser Tyr
             20                  25                  30 tgg ctg cac tgg ata aaa cag agg cct gga cag ggt ctg gaa tgg att     144
Trp Leu His Trp Ile Lys Gln Arg Pro Gly Gln Gly Leu Glu Trp Ile
         35                  40                  45 gga tac att aat cct agg aat gat tat act gag tac aat cag aac ttc     192
Gly Tyr Ile Asn Pro Arg Asn Asp Tyr Thr Glu Tyr Asn Gln Asn Phe
     50                  55                  60 aag gac aag gcc aca ttg act gca gac aaa tcc tcc agc aca gcc tac     240
Lys Asp Lys Ala Thr Leu Thr Ala Asp Lys Ser Ser Ser Thr Ala Tyr
 65                  70                  75                  80 atg caa ctg agc agc ctg aca tct gag gac tct gca gtc tat tac tgt     288
Met Gln Leu Ser Ser Leu Thr Ser Glu Asp Ser Ala Val Tyr Tyr Cys
                 85                  90                  95 gca aga agg gat att act acg ttc tac tgg ggc caa ggc acc act ctc     336
Ala Arg Arg Asp Ile Thr Thr Phe Tyr Trp Gly Gln Gly Thr Thr Leu
            100                 105                 110 aca gtc tcc tcg                                                      348
Thr Val Ser Ser
        115

<210> SEQ ID NO 4
<211> LENGTH: 116
<212> TYPE: PRT
<213> ORGANISM: Murine

<400> SEQUENCE: 4

Gln Val Gln Leu Gln Glu Ser Gly Ala Glu Leu Ser Lys Pro Gly Ala
 1               5                  10                  15

Ser Val Lys Met Ser Cys Lys Ala Ser Gly Tyr Thr Phe Thr Ser Tyr
             20                  25                  30

Trp Leu His Trp Ile Lys Gln Arg Pro Gly Gln Gly Leu Glu Trp Ile
         35                  40                  45

Gly Tyr Ile Asn Pro Arg Asn Asp Tyr Thr Glu Tyr Asn Gln Asn Phe
     50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Arg Asp Ile Thr Thr Phe Tyr Trp Gly Gln Gly Thr Thr Leu
            100                 105                 110

Thr Val Ser Ser
        115

<210> SEQ ID NO 5
<211> LENGTH: 339
<212> TYPE: DNA
<213> ORGANISM: Homo sapiens
<220> FEATURE:
```

-continued

```
<221> NAME/KEY: CDS
<222> LOCATION: (1)..(339)

<400> SEQUENCE: 5 gac att cag ctg acc cag tct cca tca tct ctg agc gca tct gtt gga        48
Asp Ile Gln Leu Thr Gln Ser Pro Ser Ser Leu Ser Ala Ser Val Gly
 1               5                  10                  15 gat agg gtc act atg agc tgt aag tcc agt caa agt gtt tta tac agt        96
Asp Arg Val Thr Met Ser Cys Lys Ser Ser Gln Ser Val Leu Tyr Ser
             20                  25                  30 gca aat cac aag aac tac ttg gcc tgg tac cag cag aaa cca ggg aaa       144
Ala Asn His Lys Asn Tyr Leu Ala Trp Tyr Gln Gln Lys Pro Gly Lys
         35                  40                  45 gca cct aaa ctg ctg atc tac tgg gca tcc act agg gaa tct ggt gtc       192
Ala Pro Lys Leu Leu Ile Tyr Trp Ala Ser Thr Arg Glu Ser Gly Val
     50                  55                  60 cct tcg cga ttc tct ggc agc gga tct ggg aca gat ttt act ttc acc       240
Pro Ser Arg Phe Ser Gly Ser Gly Ser Gly Thr Asp Phe Thr Phe Thr
 65                  70                  75                  80 atc agc tct ctt caa cca gaa gac att gca aca tat tat tgt cac caa       288
Ile Ser Ser Leu Gln Pro Glu Asp Ile Ala Thr Tyr Tyr Cys His Gln
                 85                  90                  95 tac ctc tcc tcg tgg acg ttc ggt gga ggg acc aag ctg gag atc aaa       336
Tyr Leu Ser Ser Trp Thr Phe Gly Gly Gly Thr Lys Leu Glu Ile Lys
            100                 105                 110 cgt                                                                   339
Arg

<210> SEQ ID NO 6
<211> LENGTH: 113
<212> TYPE: PRT
<213> ORGANISM: Homo sapiens

<400> SEQUENCE: 6

Asp Ile Gln Leu Thr Gln Ser Pro Ser Ser Leu Ser Ala Ser Val Gly
 1               5                  10                  15

Asp Arg Val Thr Met Ser Cys Lys Ser Ser Gln Ser Val Leu Tyr Ser
             20                  25                  30

Ala Asn His Lys Asn Tyr Leu Ala Trp Tyr Gln Gln Lys Pro Gly Lys
         35                  40                  45

Ala Pro Lys Leu Leu Ile Tyr Trp Ala Ser Thr Arg Glu Ser Gly Val
     50                  55                  60

Pro Ser Arg Phe Ser Gly Ser Gly Ser Gly Thr Asp Phe Thr Phe Thr
 65                  70                  75                  80

Ile Ser Ser Leu Gln Pro Glu Asp Ile Ala Thr Tyr Tyr Cys His Gln
                 85                  90                  95

Tyr Leu Ser Ser Trp Thr Phe Gly Gly Gly Thr Lys Leu Glu Ile Lys
            100                 105                 110

Arg

<210> SEQ ID NO 7
<211> LENGTH: 348
<212> TYPE: DNA
<213> ORGANISM: Homo sapiens
<220> FEATURE:
<221> NAME/KEY: CDS
<222> LOCATION: (1)..(348)

<400> SEQUENCE: 7 cag gtc cag ctg gtc caa tca ggg gct gaa gtc aag aaa cct ggg tca        48
```

```
Gln Val Gln Leu Val Gln Ser Gly Ala Glu Val Lys Lys Pro Gly Ser
 1               5                  10                 15 tca gtg aag gtc tcc tgc aag gct tct ggc tac acc ttt act agc tac      96
Ser Val Lys Val Ser Cys Lys Ala Ser Gly Tyr Thr Phe Thr Ser Tyr
                 20                 25                 30 tgg ctg cac tgg gtc agg cag gca cct gga cag ggt ctg gaa tgg att     144
Trp Leu His Trp Val Arg Gln Ala Pro Gly Gln Gly Leu Glu Trp Ile
            35                  40                 45 gga tac att aat cct agg aat gat tat act gag tac aat cag aac ttc     192
Gly Tyr Ile Asn Pro Arg Asn Asp Tyr Thr Glu Tyr Asn Gln Asn Phe
        50                  55                 60 aag gac aag gcc aca ata act gca gac gaa tcc acc aat aca gcc tac     240
Lys Asp Lys Ala Thr Ile Thr Ala Asp Glu Ser Thr Asn Thr Ala Tyr
 65                 70                  75                 80 atg gag ctg agc agc ctg agg tct gag gac acg gca ttt tat ttt tgt     288
Met Glu Leu Ser Ser Leu Arg Ser Glu Asp Thr Ala Phe Tyr Phe Cys
                 85                 90                 95 gca aga agg gat att act acg ttc tac tgg ggc caa ggc acc acg gtc     336
Ala Arg Arg Asp Ile Thr Thr Phe Tyr Trp Gly Gln Gly Thr Thr Val
            100                 105                110 acc gtc tcc tcg                                                     348
Thr Val Ser Ser
        115

<210> SEQ ID NO 8
<211> LENGTH: 116
<212> TYPE: PRT
<213> ORGANISM: Homo sapiens

<400> SEQUENCE: 8

Gln Val Gln Leu Val Gln Ser Gly Ala Glu Val Lys Lys Pro Gly Ser
 1               5                  10                 15

Ser Val Lys Val Ser Cys Lys Ala Ser Gly Tyr Thr Phe Thr Ser Tyr
                 20                 25                 30

Trp Leu His Trp Val Arg Gln Ala Pro Gly Gln Gly Leu Glu Trp Ile
            35                  40                 45

Gly Tyr Ile Asn Pro Arg Asn Asp Tyr Thr Glu Tyr Asn Gln Asn Phe
        50                  55                 60

Lys Asp Lys Ala Thr Ile Thr Ala Asp Glu Ser Thr Asn Thr Ala Tyr
 65                 70                  75                 80

Met Glu Leu Ser Ser Leu Arg Ser Glu Asp Thr Ala Phe Tyr Phe Cys
                 85                 90                 95

Ala Arg Arg Asp Ile Thr Thr Phe Tyr Trp Gly Gln Gly Thr Thr Val
            100                 105                110

Thr Val Ser Ser
        115

<210> SEQ ID NO 9
<211> LENGTH: 49
<212> TYPE: PRT
<213> ORGANISM: Homo sapiens

<400> SEQUENCE: 9

Pro Glu Pro Val Thr Val Ser Trp Asn Ser Gly Ala Leu Thr Ser Gly
 1               5                  10                 15

Val His Thr Phe Pro Ala Val Leu Gln Ser Ser Gly Leu Tyr Ser Leu
                 20                 25                 30

Ser Ser Val Val Thr Val Pro Ser Ser Ser Leu Gly Thr Gln Thr Tyr
            35                  40                 45
```

-continued

Ile

<210> SEQ ID NO 10
<211> LENGTH: 49
<212> TYPE: PRT
<213> ORGANISM: Homo sapiens

<400> SEQUENCE: 10

Pro Glu Pro Val Thr Val Ser Trp Asn Ser Ser Ala Leu Thr Ser Gly
 1               5                  10                  15

Val His Thr Phe Pro Ala Val Leu Gln Ser Ser Gly Leu Tyr Ser Leu
            20                  25                  30

Ser Ser Val Val Thr Val Pro Ser Ser Ser Leu Gly Thr Gln Thr Tyr
        35                  40                  45

Ile

<210> SEQ ID NO 11
<211> LENGTH: 49
<212> TYPE: PRT
<213> ORGANISM: Homo sapiens

<400> SEQUENCE: 11

Pro Glu Pro Val Thr Val Ser Trp Asn Ser Gly Ala Leu Thr Ser Gly
 1               5                  10                  15

Val His Thr Phe Pro Ala Val Leu Asn Ser Ser Gly Leu Tyr Ser Leu
            20                  25                  30

Ser Ser Val Val Thr Val Pro Ser Ser Ser Leu Gly Thr Gln Thr Tyr
        35                  40                  45

Ile

<210> SEQ ID NO 12
<211> LENGTH: 49
<212> TYPE: PRT
<213> ORGANISM: Homo sapiens

<400> SEQUENCE: 12

Pro Glu Pro Val Thr Val Ser Trp Asn Ser Gly Ala Leu Thr Ser Gly
 1               5                  10                  15

Val His Thr Phe Pro Ala Val Leu Gln Ser Ser Gly Leu Tyr Ser Asn
            20                  25                  30

Ser Ser Val Val Thr Val Pro Ser Ser Ser Leu Gly Thr Gln Thr Tyr
        35                  40                  45

Ile

<210> SEQ ID NO 13
<211> LENGTH: 49
<212> TYPE: PRT
<213> ORGANISM: Homo sapiens

<400> SEQUENCE: 13

Pro Glu Pro Val Thr Val Ser Trp Asn Ser Gly Ala Leu Thr Ser Gly
 1               5                  10                  15

Val His Thr Phe Pro Ala Val Leu Gln Ser Ser Gly Leu Tyr Ser Leu
            20                  25                  30

Ser Ser Val Val Thr Val Pro Asn Ser Ser Leu Gly Thr Gln Thr Tyr
        35                  40                  45

Ile

```
<210> SEQ ID NO 14
<211> LENGTH: 49
<212> TYPE: PRT
<213> ORGANISM: Homo sapiens

<400> SEQUENCE: 14
```

Pro Glu Pro Val Thr Val Ser Trp Asn Ser Gly Ala Leu Thr Ser Gly
 1               5                  10                  15

Val His Thr Phe Pro Ala Val Leu Gln Ser Ser Gly Leu Tyr Ser Leu
            20                  25                  30

Ser Ser Val Val Thr Val Pro Ser Ser Asn Gly Thr Gln Thr Tyr
        35                  40                  45

Ile

```
<210> SEQ ID NO 15
<211> LENGTH: 53
<212> TYPE: PRT
<213> ORGANISM: Homo sapiens

<400> SEQUENCE: 15
```

Pro Arg Glu Ala Lys Val Gln Trp Lys Val Asp Asn Ala Leu Gln Ser
 1               5                  10                  15

Gly Asn Ser Gln Glu Ser Val Thr Glu Gln Asp Ser Lys Asp Ser Thr
            20                  25                  30

Tyr Ser Leu Ser Ser Thr Leu Thr Leu Ser Lys Ala Asp Tyr Glu Lys
        35                  40                  45

His Lys Val Tyr Ala
    50

```
<210> SEQ ID NO 16
<211> LENGTH: 53
<212> TYPE: PRT
<213> ORGANISM: Homo sapiens

<400> SEQUENCE: 16
```

Pro Arg Glu Ala Lys Val Gln Trp Lys Val Asp Asn Ala Ser Gln Ser
 1               5                  10                  15

Gly Asn Ser Gln Glu Ser Val Thr Glu Gln Asp Ser Lys Asp Ser Thr
            20                  25                  30

Tyr Ser Leu Ser Ser Thr Leu Thr Leu Ser Lys Ala Asp Tyr Glu Lys
        35                  40                  45

His Lys Val Tyr Ala
    50

```
<210> SEQ ID NO 17
<211> LENGTH: 53
<212> TYPE: PRT
<213> ORGANISM: Homo sapiens

<400> SEQUENCE: 17
```

Pro Arg Glu Ala Lys Val Gln Trp Lys Val Asp Asn Ala Leu Gln Ser
 1               5                  10                  15

Gly Asn Ser Gln Glu Ser Val Thr Glu Gln Asp Ser Lys Asp Ser Thr
            20                  25                  30

Tyr Ser Leu Ser Ser Thr Leu Asn Leu Ser Lys Ala Asp Tyr Glu Lys
        35                  40                  45

His Lys Val Tyr Ala
    50

```
<210> SEQ ID NO 18
<211> LENGTH: 53
<212> TYPE: PRT
<213> ORGANISM: Homo sapiens

<400> SEQUENCE: 18

Pro Arg Glu Ala Lys Val Gln Trp Lys Val Asp Asn Ala Leu Gln Ser
 1               5                  10                  15

Gly Asn Ser Asn Glu Ser Val Thr Glu Gln Asp Ser Lys Asp Ser Thr
                20                  25                  30

Tyr Ser Leu Ser Ser Thr Leu Thr Leu Ser Lys Ala Asp Tyr Glu Lys
            35                  40                  45

His Lys Val Tyr Ala
        50

<210> SEQ ID NO 19
<211> LENGTH: 53
<212> TYPE: PRT
<213> ORGANISM: Homo sapiens

<400> SEQUENCE: 19

Pro Arg Glu Ala Lys Val Gln Trp Lys Val Asp Asn Ala Leu Gln Ser
 1               5                  10                  15

Gly Asn Ser Gln Glu Ser Val Thr Glu Gln Asp Ser Lys Asp Ser Thr
                20                  25                  30

Tyr Asn Leu Ser Ser Thr Leu Thr Leu Ser Lys Ala Asp Tyr Glu Lys
            35                  40                  45

His Lys Val Tyr Ala
        50

<210> SEQ ID NO 20
<211> LENGTH: 113
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Val Leu Tyr Ser
                20                  25                  30

Ala Asn His Lys Asn Tyr Leu Ala Trp Tyr Gln Gln Thr Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Tyr Thr Phe Thr
 65                 70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gln Gly Thr Lys Leu Gln Ile Thr
            100                 105                 110

Arg

<210> SEQ ID NO 21
<211> LENGTH: 116
<212> TYPE: PRT
<213> ORGANISM: Homo sapiens

<400> SEQUENCE: 21
```

```
Gln Val Gln Leu Gln Gln Ser Gly Ala Glu Val Lys Lys Pro Gly Ser
  1               5                  10                  15

Ser Val Lys Val Ser Cys Lys Ala Ser Gly Tyr Thr Phe Thr Ser Tyr
             20                  25                  30

Trp Leu His Trp Val Arg Gln Ala Pro Gly Gln Gly Leu Glu Trp Ile
         35                  40                  45

Gly Tyr Ile Asn Pro Arg Asn Asp Tyr Thr Glu Tyr Asn Gln Asn Phe
     50                  55                  60

Lys Asp Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Phe Tyr Phe Cys
                 85                  90                  95

Ala Arg Arg Asp Ile Thr Thr Phe Tyr Trp Gly Gln Gly Thr Thr Val
            100                 105                 110

Thr Val Ser Ser
        115

<210> SEQ ID NO 22
<211> LENGTH: 149
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
tataatcatt cctaggatta atgtatccaa tccattccag accctgtcca ggtgcctgcc      60
tgacccagtg cagccagtag ctagtaaagg tgtagccaga agccttgcag gagaccttca    120
ctgatgaccc aggtttcttg acttcagcc                                      149

<210> SEQ ID NO 23
<211> LENGTH: 140
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 23
ccccagtaga acgtagtaat atcccttctt gcacaaaaat aaaatgccgt gtcctcagac      60
ctcaggctgc tcagctccat gtaggctgta ttggtggatt cgtctgcagt tattgtggcc    120
ttgtccttga agttctgatt                                                140

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 24
ccagctgcag caatcagggg ctgaagtcaa gaaacctg                              38

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: synthetic
      oligonucleotide
```

<400> SEQUENCE: 25
aagtggatcc tataatcatt cctaggatta atg            33

<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 26
taatcctagg aatgattata ctgagtacaa tcagaacttc aaggaccag            49

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 27
ggagacggtg accgtggtgc cttggcccca gtagaacgta gtaa            44

<210> SEQ ID NO 28
<211> LENGTH: 150
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 28
cctagtggat gcccagtaga tcagcagttt aggtgctttc cctggtttct ggtggtacca      60
ggccaagtag ttcttgtgat ttgcactgta taaaacactt tgactggact tacagctcat    120
agtgacccta tctccaacag atgcgctcag            150

<210> SEQ ID NO 29
<211> LENGTH: 52
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 29
gacaagcttc agctgaccca gtctccatca tctctgagcg catctgttgg ag            52

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 30
agagaatcgc gaagggacac cagattccct agtggatgcc cagta            45

<210> SEQ ID NO 31
<211> LENGTH: 121
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 31
ccagcttggt ccctccaccg aacgtccacg aggagaggta ttggtgacaa taatatgttg    60
caatgtcttc tggttgaaga gagctgatgg tgaaagtaaa atctgtccca gatccgctgc   120
c                                                                    121

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 32
gacaagcttt cgcgattctc tggcagcgga tctgggacag                           40

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 33
gaccggcaga tctgcaccTT ggtccctcca ccg                                  33

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 34
ccaatcgggt aattcgaatg agagtgtcac agag                                 34

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 35
ggacagcacc tacaacttaa gcagcaccct gac                                  33

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 36
ggaaggtgga taacgcgtcc caatcgggta a                                    31

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 37
agcagcaccc taaatttgag caaagcagac t                                31

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 38
gagtgtcaca gagaacgtta gcaaggacag cacc                             34

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 39
gtgtcgtgga actcaagcgc tctgaccagc ggc                              33

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 40
ttcccggctg tcctgaattc ctcaggactc tact                             34

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 41
cctcaggact ctactcgaat tccagcgtgg tgaccgt                          37

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 42
gtggtgaccg tcccgaattc cagcttgggc acc                              33

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 43
gccctccagc agcaacggta cccagaccta catctgc                          37

<210> SEQ ID NO 44

```
-continued

<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 44
acggtatcga tatgcatgat atcgaatt                                   28

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 45
gtgtcgtgga attcaaccgc cctgaccagc ggc                             33

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 46
gtgtcgtgga attcaggcaa cctgaccagc ggc                             33

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 47
tggaactcag gcgcgaatac cagcggcgtg cac                             33
```

GLYCOSYLATED HUMANIZED B-CELL SPECIFIC ANTIBODIES

RELATED APPLICATIONS

This application is a national stage application under 35 U.S.C. §371 of PCT/US97/04196 filed on Mar. 19, 1997, which claims priority to U.S. Ser. No. 60/013,709 filed on Mar. 20, 1996.

BACKGROUND OF THE INVENTION

The invention relates generally to immunoconjugates for diagnostic and therapeutic uses in cancer. In particular, the invention relates to recombinantly produced humanized monoclonal antibodies directed against B-cell lymphoma and leukemia cells, which antibodies can be covalently conjugated to a diagnostic or therapeutic reagent without loss of antibody binding and internalization function and with reduced production of human anti-mouse antibodies.

Non-Hodgkins lymphoma (NHL) and chronic lymphocytic leukemia are B-cell malignancies that remain important contributors to cancer mortality. The response of these malignancies to various forms of treatment is mixed. They respond reasonably well to chemotherapy, and, in cases where adequate clinical staging of NHL is possible, as for patients with localized disease, satisfactory treatment may be provided using field radiation therapy (Hall et al., *Radiology for the Radiologist*, Lippincott, Philadelphia, 1989, pp 365–376). However, the toxic side effects associated with chemotherapy and the toxicity to the hematopoietic system from local, as well as whole body, radiotherapy, limits the use of these therapeutic methods. About one-half of the patients die from the disease (Posner et al., *Blood*, 61: 705 (1983)).

The use of targeting monoclonal antibodies conjugated to radionuclides or other cytotoxic agents offers the possibility of delivering such agents directly to the tumor site, thereby limiting the exposure of normal tissues to toxic agents (Goldenberg, *Semin. Nucl. Med.*, 19: 332 (1989)). In recent years, the potential of antibody-based therapy and its accuracy in the localization of tumor-associated antigens have been demonstrated both in the laboratory and clinical studies (see., e.g., Thorpe, *TIBTECH*, 11: 42 (1993); Goldenberg, *Scientific American, Science & Medicine*, 1: 64 (1994); Baldwin et al., U.S. Pat. Nos. 4,925,922 and 4,916,213; Young, U.S. Pat. No. 4,918,163; U.S. Pat. No. 5,204,095; Irie et al., U.S. Pat. No. 5,196,337; Hellstrom et al., U.S. Pat. Nos. 5,134,075 and 5,171,665). In general, the use of radio-labeled antibodies or antibody fragments against tumor-associated markers for localization of tumors has been more successful than for therapy, in part because antibody uptake by the tumor is generally low, ranging from only 0.01% to 0.001% of the total dose injected (Vaughan et al., *Brit. J. Radiol.*, 60: 567 (1987)). Increasing the concentration of the radiolabel to increase the dosage to the tumor is counterproductive generally as this also increases exposure of healthy tissue to radioactivity.

LL2 (EPB2) is a highly specific anti-B-cell lymphoma and anti-lymphocytic leukemia cell murine monoclonal antibody (mAb) that is rapidly internalized by such cells and that can overcome some of the aforementioned difficulties (Shih et al., *Int. J. Cancer*, 56: 538 (1994)). LL2, which is of the IgG2a antibody type, was developed using the Raji B-lymphoma cell line as the source of antigen (Pawlak-Byczkowska et al., *Cancer Res.*, 49: 4568 (1989)). Murine LL2 (mLL2) is known to react with an epitope of CD22 (Belisle et al., *Proc Amer. Assn. Clin. Res.*, 34: A2873 (1993)). CD22 molecules are expressed in the cytoplasm of progenitor and early pre-B cells, and appear in the cell surface of mature B-cells.

By immunostaining of tissue sections, mLL2 was shown to react with 50 of 51 B-cell lymphomas tested. mLL2 provides a highly sensitive means of detecting B-cell lymphoma cell in vivo, as determined by a radioimmunodetection method (Murthy et al., *Eur. J. Nucl. Med.*, 19: 394 (1992)). The Fab' fragment of mLL2 labeled with $^{99m}$Tc localized to 63 of 65 known lesions in Phase II trial patients with B-cell lymphoma (Mills et al., *Proc. Amer. Assn. Cancer Res.*, 14: A2857 (1993)). In addition, $^{131}$I-labeled mLL2 was therapeutically effective in B-cell lymphoma patients (Goldenberg et al., *J. Clin. Oncol.*, 9: 548 (1991)). mLL2 Fab' conjugated to the exotoxin PE38KDEL induced complete remission of measurable human lymphoma xenografts (CA-46) growing in nude mice (Kreitman et al., *Cancer Res.*, 53: 819 (1993)).

The clinical use of mLL2, just as with most other promising murine antibodies, has been limited by the development in humans of a human anti mouse antibody response (HAMA). While a HAMA response is not invariably observed following injection of mLL2, in a significant number of cases patients developed HAMA following a single treatment with mLL2. This can limit the diagnostic and therapeutic usefulness of such antibody conjugates, not only because of the potential anaphylactic problem, but also as a major portion of the circulating conjugate may be complexed to and sequestered by the circulating anti-mouse antibodies. This is exemplified by one study in which about 30% of the patients developed low level HAMA response following a single injection of about 6 mg of mLL2 $^{131}$I-IgG and nearly all developed a strong HAMA response with additional injections. On the other hand, with mLL2 Fab' labeled with $^{99m}$Tc, no HAMA response was observed. Such HAMA responses in general pose a potential obstacle to realizing the full diagnostic and therapeutic potential of the mLL2 antibody.

As noted above, the use of fragments of mLL2, such as F(ab')$_2$ and Fab', partially alleviates/circumvents these problems of immunogenicity. However, there are circumstances in which whole IgG is more desirable, such as when induction of cellular immunity is intended for therapy, or where an antibody with enhanced survival time is required.

For monoclonal antibodies to function as the delivery vehicles for drugs and radionuclides, it is of prime importance to develop methods for their site-specific conjugations, with minimal perturbation of the resultant immunoreactivities. Most commonly, the conjugation of drugs and radionuclides are accomplished through their covalent attachments to side chains of amino acid residues. Due to the non-site-restricted nature of these residues, it is difficult to avoid undesirable couplings at residues that lie within or are in close vicinity to the ABS, leading to reduced affinity and heterogenous antigen-binding properties. Alternatively, conjugation can be directed at sulfhydryl groups. However, direct labeling relies on the reduction of S-S bonds, with the possible risk of protein fragmentation.

U.S. patent application Ser. No. 08/289,576, now abandoned, but refiled as continuation application, U.S. patent application Ser. No. 08/690,102, now U.S. Pat. No. 5,789,554, issued on Aug. 4, 1998, the entire disclosure of which is incorporated herein by reference, discloses a humanized mAb having a naturally occurring N-linked glycosylation site found at amino acid positions 18–20 of the LL2 VK domain for site-specific drug or chelate conjugation. The attached carbohydrate moiety was positioned away from, and demonstrated no physical contacts with, the antigen binding site (ABS). The immunoreactivity of the antibody was not affected when chelates such as DTPA were conjugated to the carbohydrate.

However, there are limitations to the usefulness of this antibody. For one, it is not clear what size and type of chelates can be attached before immunoreactivity is affected. We have determined that attachment of larger chelates does affect the binding affinity. Thus, attachment of an 18 kD Dox-dextran to the carbohydrate at position 18–20 of the LL2 VK domain reduces immunoreactivity to about 50%. Furthermore, it would be very advantageous to engineer other antibodies to contain active glycosylation sites. Engineering other antibodies so that glycosylation sequences are present in the variable region is difficult because the engineering steps would need to be repeated for each antibody. Furthermore, the immunoreactivity of the construct might be affected.

IgG glycosylation at Asn-297 in the CH2 Fc domain has been well-characterized as important for the maintenance of antibody stability and the appropriate structure for proper effector functions. See Tao and Morrison, *J. immunol.* 143: 2595 (1989). Due to the restricted localization of immunoglobulin glycosylation sites, which are distal to the ABS, oligosaccharide modification of monoclonal antibodies was used to prepare conjugates. Conjugates modified with $^{131}I$ coupled to a tyrosine-containing peptide, which was then site-specifically attached to oxidized oligosaccharides, exhibited greater targeting efficiency compared to the conjugates that were modified nonselectively on tyrosine. Because the use of Asn-297-associated carbohydrate requires the presence of the Fc portion of the antibody, its use is limited. There are certain applications employing antibody fragments in which the Fc portion is not present.

SUMMARY OF THE INVENTION

The present invention extends those approaches by engineering N-linked glycosylation sites into the Constant-kappa (CK), a constant light chain domain and the constant-heavy (CH1) domains. This has the following advantages:

1. glycosylation will be on a different domain which is physically more distant from the variable domains constituting the ABS;
2. high dosage conjugation of chelates or even bulky groups which might affect the fine structure of the CK or CH1 domain would be expected to have minimal effects, if any, on the VH and VX domains forming the ABS;
3. antibody fragments, a preferred format in some clinical applications, contain both the CH1 and CK domains, and the conjugation site should be suitable for use in antibody fragments (e.g., Fab, F(ab')$_2$);
4. unlike the VK-appended glycosylation site which would have to be introduced (e.g. by site-directed mutagenesis) into different antibodies on a case-by-case basis, the CK or CH1 domain containing the carbohydrate addition sites, once identified as an efficient conjugation handle, can easily be ligated to different variable domains having different antigen specificities.

It is an object of this invention to provide humanized antibodies, having glycosylation in the CK or CH1, domains, that retain antigen binding specificity.

It is another object of this invention to provide conjugates of the glycosylated mabs containing therapeutic or diagnostic modalities.

It is a further object of this invention to provide methods of therapy and diagnosis that utilize the humanized mAbs of the invention.

In order to achieve these objectives, in one aspect of the invention, a monoclonal antibody or antibody fragment which is engineered to contain a glycosylation site in the non-Fc constant heavy-chain or light-chain region has been provided. In a preferred embodiment, the monoclonal antibody or antibody fragment is a humanized antibody or antibody fragment. In another preferred embodiment, the humanized specific monoclonal antibody is a humanized B-cell specific antibody or antibody fragment. In yet another preferred embodiment, the glycosylation is located on a site selected from the group consisting of the HCN1, HCN2, HCN3, HCN4, and HCN5 sites of FIG. 12. In particularly preferred embodiments, the glycosylation site is the HCN5 site or the HCN1 site of FIG. 12. In a further preferred embodiment, the antibody which is engineered to contain a glycosylation site is an antibody having the specificity of the hLL2 antibody.

In another aspect of the invention, an isolated DNA molecule comprising an antibody heavy chain gene which comprises a sequence within the CH1 region has been provided, which, when the gene is coexpressed with a second gene for an antibody light chain in a cell supporting glycosylation, will produce an antibody glycosylated in the CH1 region.

In a further aspect, an isolated DNA molecule comprising an antibody light chain gene which comprises a sequence within the constant region has been provided, which, when said gene is coexpressed with a second gene for an antibody heavy chain in a cell supporting glycosylation, will produce an antibody glycosylated in the constant K region.

In a yet further aspect of the invention, a method of producing an antibody or antibody fragment glycosylated in the constant K and/or CH1 region has been provided comprising coexpressing light and heavy chain genes or portions thereof, which have been engineered with a mutation such that a glycosylation site is created in the constant K region or into the CH1 region of said heavy chain gene or portions thereof, in a cell that allows glycosylation, such that the antibody or antibody fragment glycosylated in the constant K and/or CH1 region is produced, and isolating the antibody or antibody fragment.

In a further still aspect of the invention, a method of diagnosis or treatment of a patient has been provided, wherein a monoclonal antibody or antibody fragment is used to target a specific antigen, the antibody or fragment being used as such or conjugated to a diagnostic or therapeutic agent, the improvement wherein said antibody or fragment is a humanized monoclonal antibody or antibody fragment engineered to contain a glycosylation site in the non-Fc constant heavy-chain or light-chain region. In a preferred embodiment, the antibody or antibody fragment is a B-cell specific antibody or antibody fragment.

BRIEF DESCRIPTION OF THE DRAWINGS

FIG. 1 shows a comparison of murine and humanized LL2 VK (FIG. 1A, SEQ ID NOS 2, 6 & 20) and VH (FIG. 1B, SEQ ID NOS 4, 21 & 8) domains. Only hFR sequences (designated as REIHuVK and EUHuVH) different than mFR sequences (designated as murine) are shown, and designated by asterisks. CDRs are boxed. FR residues shown by computer modeling to contact a CDR are underlined.

FIG. 2 shows the vicinal relationships of LL2 CDRs to their framework regions (FRs). Separate energy-minimized models for the VL and VH domains of mLL2 were constructed, and all FR residues within a radius of 4.5 Å or any CDR atom were identified as potential CDR-FR contacts. CDRs of the light (L1, L2, and L3, FIG. 2A) and heavy (H1, H2, and H3, FIG. 2B) chains are shown as "ball and stick" representations superimposed on their respective, space-filling FRs.

FIG. 3A shows the light chain staging (VKpBR) and mammalian expression (pKH) vectors, and FIG. 3B shows the heavy chain staging (VHpBS) and mammalian expression (pG1g) vectors.

FIG. 4 shows the double-stranded DNA and amino acid sequences of the LL2 VK domain (FIG. 4A, SEQ ID NOS 1 & 2) and the LL2 VH domain (FIG. 4B, SEQ ID NOS:3 & 4). Amino acid sequences encoded by the corresponding DNA sequences are given as one letter codes. CDR amino acid sequences are boxed. The Asn-glycosylation site located in FR1 of LL2VK (FIG. 4A) is shown as the underlined NVT sequence.

FIG. 5A shows the double stranded DNA and corresponding amino acid residues of the hLL2 VK domain (SEQ ID NOS 5 & 6). CDR amino acid sequences are boxed. The corresponding data for the VH domain (SEQ ID NOS 7 & 8) is shown in FIG. 5B.

FIG. 6 is a schematic diagram representation of the PCR/gene synthesis of the humanized VH region and the subcloning into the staging vector, VHpBS.

Figure 12:
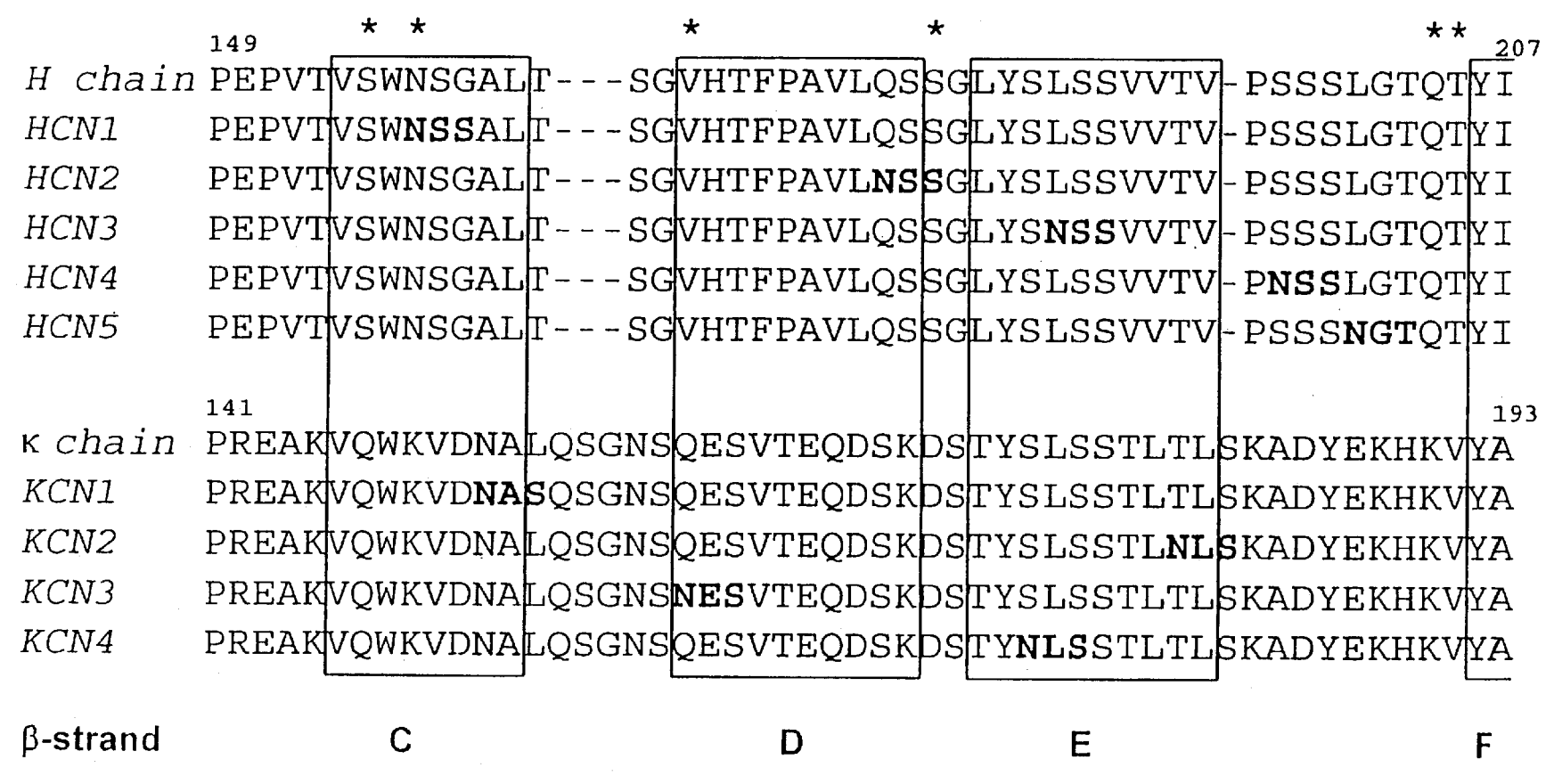
Figure 2A:
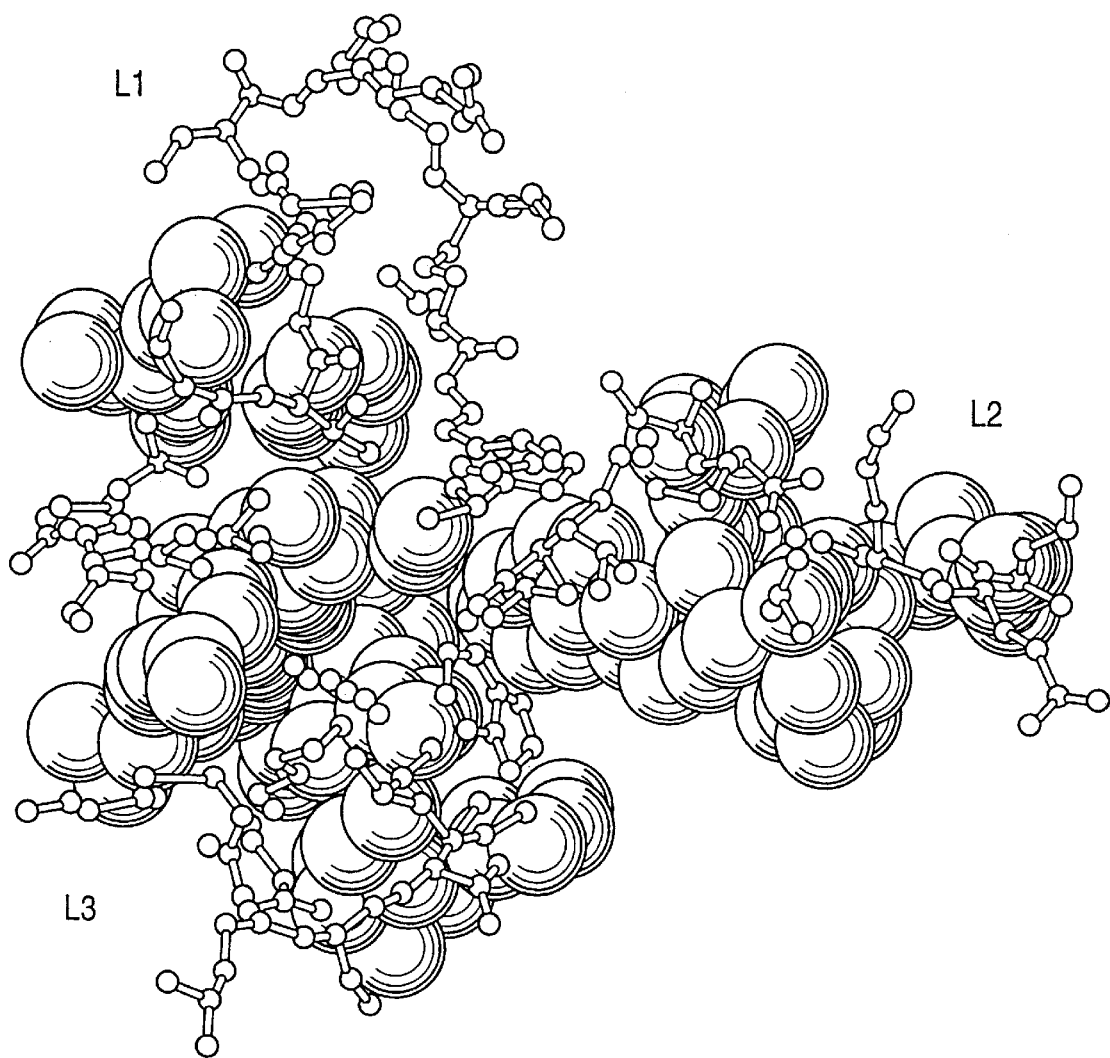

FIG. 12 shows the N-glycan acceptor sequences and positions introduced into the $CH_1$ and $C\kappa$ domains of hLL2 (SEQ ID NOS 9–10). Site-directed mutagenesis were used to generate the tri-peptide acceptor sequences (shown in bold letters). Partial peptide sequences of the $CH_1$ (H chain) and $C\kappa$ (κ chain) domains of hLL2 are shown and aligned according to sequence and structure homology to indicate the locations of engineered potential N-linked glycosylation sites (HCN1–HCN5 and KCN1–KCN4). The β-strand sequences (C–F) are boxed. The residues were numbered according to Kabat's system; asterisk (*) indicate these heavy chain aa residues which were numbered discontinuously from the previous aa residue. The aa residues indicated by * are numbered, from left to right, as 156, 162, 171, 182, 203, and 205, respectively.

DETAILED DESCRIPTION OF THE PREFERRED EMBODIMENTS

Glycosylation sites are engineered into CK and CH1 immunoglobulin domains to provide humanized immuno-globulin with engineered glycosylation sites. By using site-directed mutagenesis, glycosylation sites are engineered into the constant regions of the heavy and light chains, specifically into the CK and CH1 domains. The mutated CK and CH1 nucleotide sequences are then subcloned into light and heavy chain expression vectors, respectively. The CH1 mutated heavy chain expression vector is coexpressed with a light chain expression vector to produce mutated, humanized antibodies with altered glycosylation sites in the CH1 domain. A similar procedure is followed to produce mutated humanized antibodies with altered glycosylation sites in the CK domain.

It should be noted that not all potential carbohydrate-addition sequences can be used for oligosaccharide attachment. A series of glycosylation mutants were generated by introducing novel N-linked glycosylation sequences at the heavy chain complementarity determining region 2 (CDR2) region of anti-dextran and anti-dansyl antibodies, respectively. While glycosylation as found at Asn 54 and Asn 60 of the anti-dextran antibody, the carbohydrate addition site placed in a similar position (Asn 55) in the anti-dansyl antibody, however, was not utilized. This "position effect" is not well understood, but is most likely to be related to the protein conformation and accessibility of the carbohydrate acceptor sequence to glycolyl-transferase.

In this specification, the expressions "hLL2" or "hLL2 mAb" are intended to refer to the monoclonal antibody constructed by joining or subcloning the complementarity determining regions (CDRs) of murine VK and VH regions to human framework regions (FRs) and joining or subcloning these to human constant light and heavy chains, respectively.

Covalent conjugates between the mutated antibodies of the invention and a diagnostic or chemotherapeutic reagent, formulated in pharmaceutically acceptable vehicles (see, e.g., *Remington's Pharmaceutical Sciences*, 18th ed., Mack Publishing Co., Easton, Pa., 1990) can be prepared. B cell lymphoma and leukemia specific antibodies comprising glycosylated CK and CH1 domains conjugated to a diagnostic or therapeutic reagent resulting in humanized mAbs continue to have the ability to internalize into target cells, and to rapidly liberate the diagnostic or chemotherapeutic reagent intracellularly (thereby increasing effectiveness of the reagent), and the added advantage of a reduction of the HAMA response in the human patient.

Since the carbohydrate moiety of the engineered antibodies of the invention is not involved in the binding of the antigen, conjugates in which a reagent is bound to the antibody through carbohydrate moieties can be used. For example, a reagent can be conjugated to an oxidized carbohydrate derivative. Methods for the production of such conjugates, and their use in diagnostics and therapeutics are provided, for example, in Shih et al., U.S. Pat. No. 5,057,313, Shih et al., *Int. J. Cancer* 41: 832 (1988), and copending, commonly owned Hansen et al., U.S. Ser. No. 08/162,912, now U.S. Pat. No. 5,443,953, issued on Aug. 22, 1995, the contents of which are incorporated herein by reference. Direct linkage of a reagent to oxidized carbohydrate without the use of a polymeric carrier is described in McKearn et al., U.S Pat. No. 5,156,840, which is also incorporated by reference.

A wide variety of diagnostic and therapeutic reagents can be advantageously conjugated to the antibodies of the invention. These include: chemotherapeutic drugs such as doxorubicin, methotrexate, taxol, and the like; chelator, such as DTPA, to which detectable labels such as fluorescent molecules or cytotoxic agents such as heavy metals or radionuclides can be complexed; and toxins such as Pseudomonas exotoxin, and the like. Several embodiments of these conjugates are described in the examples below.

Additional or alternative glycosylation sites (NXT/S) can be designed and introduced into the Vk, Ck and CH domains of any antibody according to the invention, for example hLL2 (here X stands for any amino acid but proline or aspartate). The effects on binding specificity, biodistribution in vivo, in test animals, and efficiency of conjugation of drugs and chelates of the glycosylated moieties can be assayed to determine useful glycosylation sites. Likely sites for glycosylation may be identified by comparison with glycosylation sites from known Ab of different species or isotypes, by analysis of the known structures of human CK and CH1 domains by computer modeling to identify exposed positions, or by random shot-gun mutagenesis.

Cell lines and culture media used in the present invention include LL2 (EPB-2) hybridoma cells (Pawlak-Byczkowska et al. 1989 above), Sp2/0-Ag12 myeloma cells (ATCC, Rockville, Md.) and Raji cells. These cells are preferably cultured in Dulbecco's modified Eagle's Medium (DMEM) supplemented with 10% FCS (Gibco/BRL, Gaithersburg, Md.), 2 mM L-glutamine and 75 µg/ml gentamicin, (complete DMEM). Transfectomas are grown in Hybridoma Serum Free Medium, HSFM, (Gibco/BRL, Gaithersburg, Md.) containing 10% of FCS and 75 µg/ml gentamicin (complete HSFM) or, where indicated, in HSFM containing only antibiotics. Selection of the transfectomas may be carried out in complete HSFM containing 500 µg/ml of hygromycin (Calbiochem, San Diego, Calif.). All cell lines are preferably maintained at 37° C. in 5% $CO_2$.

Designing Glycosylation Sites in CH1 and CK

An important aspect of this invention is that antibody conformations can be modeled by computer modeling (see, for example, Dion, in Goldenberg et al. eds., *Cancer Therapy With Radiolabelled Antibodies*, CRC Press, Boca Raton, Fla., 1994), which is incorporated by reference. In general, the 3-D structures are best modeled by homology, which is facilitated by the availability of crystallographic data from the Protein Data Bank (PDR Code 1REI, Bernstein et al., *J. Mol. Biol.* 112: 535 (1977)), which is incorporated by reference. Similarly, the antibody EU (VH) sequences (Kabat et al., SEQUENCES OF PROTEINS OF IMMUNOLOGICAL INTEREST, 5th edition, U.S. Dept. of Health and Human Services, U.S. Gov. Printing Office (1991)) can be selected as the modeling counterparts for FR1 to FR3 of the mLL2 heavy chain; FR4 was based on NEWM. Id. As X-ray coordinate data is currently lacking for the EU sequence, NEWM structural data (PDR Code 3FAB) for FRs 1 to 4 can be used, and amino acid side groups can be replaced to correspond to mLL2 or EU (hLL2) as needed. The CDR of the light chain can be modeled from the corresponding sequence of 1MCP Protein Data Bank (L1 and L2) and 1REI (L3). For heavy chain CDRs, H1 and H2 can be based on 2HFL Protein Data Bankand 1MCP, respectively, while H3 can be modeled de novo. Wherever possible, side group replacements should be performed so as to maintain the torsion angle between $C\alpha$ and $C\beta$. Energy minimization may be accomplished by the AMBER forcefield (Weiner et al, *J. Amer. Chem. Soc.* 106: 765 (1984) using the convergent method. Potentially critical FR-CDR interactions can be determined by initially modeling the light and heavy variable chains of mLL2. All FR residues within a 4.5 Å radius of all atoms within CDRs can thereby be identified and retained in the final design model of hLL2.

The homologous molecular model of Fab fragment of hLL2 was created with QUANTA protein modeling package using the x-ray structure of humanized anti-pl85her2 antibody fragments (1FVD) as main template. See Carter et al., *Proc. Natl. Acad. Sci.* 89: 4285 (1992); Eizenbrot et al., *J. Mol. Biol.* 229: 969 (1993). The sequence identity between the two antibodies is about 80%. The insertion regions were modeled by searching available protein data libraries. After all coordinates were generated and connection regions were regularized, a series of energy minimizations were applied to the model. This includes 100 step Steepest descent (SD) and Conjugated Gradient (CG) EM for side chain atoms only, then 100 step SD and CG EM for all except $C\alpha$ atoms and finally 100 step SD and EM for all atoms. A distance related dielectric constant, 4r (r is the atom-atom distance in Å) was used for electrostatic interactions. The RMS of atomic position for equivalent main chain and side chain atoms between 1FVD and hLL2 were 1.46 Å and 2.11 Å, respectively. Point mutations were then applied to hLL2 to generate the models of mutant antibodies, hLL2HCN1 and hLL2HCN5. Complex-type oligosaccharides were modeled using the same program with the compositions and structures elucidated from carbohydrate sequencing.

Each generated oligosaccharide chain was then anchored to the corresponding N-linked glycosylation site with the 01 of the terminal GlcNac superimposed to the $N_d$ of the Asn and 01C1 bond of the GlcNac co-lined with one of Nd—H bonds of the Asn. The conformation of the attached oligosaccharide chain was sequentially manipulated so that the longest branch was close to the variable region of the heavy chain of hLL2. After each adjustment, 100 step SD and CG EM were applied to sugar atoms with fixed anchor atoms and hLL2 atoms.

The designs for the CK and CH1 glycosylation sites are based on the following principles:

1. A carbohydrate-addition-site with the sequence NXS/T was chosen. X can be any amino acids except Proline and Aspartate. Whenever possible, only single amino acid changes to install potential glycosylation sites at a chosen position were attempted so as to minimize perturbation of the domain structure.
2. Potential CK or CH1-associated glycosylation sites can be identified from known antibodies sequence of different species or isotypes.
3. Analyses of the known structures of human CK and CH1 domains by computer modeling to identify exposed positions where potential Asn-glycosylation sites can be planted.

Based on computer modeling studies, the closest approach distance between the VK-appended oligosaccharide and the CDRs was estimated to be 20 Å. A distance greater than 4.1 Å is considered to be free of interactions. Thus, glycosylation sites which are 4.1 Å or further away from the antigen binding site are likely candidates for use as conjugation sites for antibody fragments. Whenever possible, the mutations introduced into the CH1 and CK domains are conservative in nature, so as to maintain the final tertiary structure of the protein domains. A conservative mutation generally involves substitution of one for another by similar size and clinical properties. specifically, the desired sequence is NXT/S. For example, replacement of a glutamine (Q) in the original sequence with asparagine (N) would be considered a conservative substitution. In this way, various CH1 and CK domain mutations can be designed to produce inventive glycosylation sites.

Only exposed sites will have the chance of being glycosylated. Therefore, computer modeling to help locating additional sites that are at potentially favorable positions was employed. The glycosylation site HCN5 was predicted to be farther away from the ABS and at the surface position; HCN5 site is located at the bottom loop formed between the E and F-stands. Other sites, which are "evenly" dispersed along the CK and CH1, domains sequences, were randomly selected. In all cases, possible perturbations in the final tertiary structure were minimized by carefully choosing sequences that required only one single amino acid substitution to become potential glycosylation site. A total of five CH1, (HCN1–5) and four Cκ (KCN1–4)-appended sites were introduced to the $CH_1$, and Cκ domains, respectively. None of these sites appeared to be "buried," or at the interface between two juxtaposed domains, as confirmed by computer modeling analyses.

N-glycosylation was described only as an example. The principles involved are equally applicable to O-glycosylation. An artisan skilled in the art would readily understand the application of the modeling, the design of glycosylation sites, and alteration of constant K, CH, and VK regions, to allow for O-glycosylation. O-glycosylation is known to occur at either threoine or serine. The acceptor sequence for O-linked glycosylation is relatively ill defined (Wilson et al., *Biochem. J.* 275: 526 (1991). There could be a bias for higher content of proline, serine and threonine in these regions, but accessibility, rather than the exact primary sequence determines whether a particular threonine or serine residue will be O-glycosylated. Nevertheless, potential O-glycosylation sequences, such as those identified in other antibodies known to have O-glycosylation (Chandrashekarkan et al., *J. Biol. Chem.* 259: 1549 (1981); Smyth and Utsumi, *Nature* 216: 322 (1967); Kim et al., *J. Biol. Chem.* 269: 12345 (1994), can be used as the standard sequences for grafting into different positions in the antibodies of interest. Those confirmed to contain extensive O-glycosylation can then be tested as conjugation site.

Another important aspect of the invention is that once a glycosylation site is identified, further identification of other potential glycosylation sites is made easier. This is due to two phenomena. For one, successful glycosylation confirms and helps further refine the modeling of the relevant regions. Secondly, the constant K and CH1 regions are understood to display considerable symmetry. Therefore, identification of a site where glycosylation occurs on, say CH1, leads to an expectation that the equivalent CK, position would be a good glycosylation site.

Light chain mutations.

Potential N-linked glycosylation sequences have been identified in the kappa constant regions of rabbit antibodies at aa position 161–163 and 174–176. Similar sites can be introduced into the CK domain of hLL2. See FIG. 12 for examples.

Heavy chain mutations.

In CH1, a carbohydrate-addition-sequence, Asn-Asn-Ser, has been identified at a.a. positions 161–163 (Kabat's numbering; Kabat et al., 1991) in some of the human IgM CH1 domains. Similarly, the sequence Asn-Val-Thr, was positioned in a.a. positions 168–170 in the CH1 domain of human IgA. Examples of sequences which can be modified to produce altered glycosylation sites are: mutating the human IgG1 sequence Asn-Ser-Gly to Asn-Ser-Val at a.a. positions 162–164, Ala-Leu-Thr to Asn-Leu-Thr at a.a. positions 165–167, and Leu-Thr-Ser to Asn-Thr-Ser at a.a. positions 166–168, respectively. These three potential N-linked glycosylation sites, are analogous to that of IgM and IgA and can be introduced into the CH1 domain of human IgG1, with expectation of minimal interference on the resultant structure. Such glycosylation sites may thus remain in a "natural" position. The design of similar mutations is well within one of skill in the art, based on the teachings in the specification.

Site-directed mutagenesis

Detailed protocols for oligonucleotide-directed mutagenesis and related techniques for mutagenesis of cloned DNA are well-known. For example, see Sambrook et al., supra, and Ausubel et al., supra.

Asn-linked glycosylation sites may be introduced into antibodies using conventional site-directed oligonucleotide mutagenesis reactions. For example, to introduce an Asn in position 18 of a kappa protein, one may alter codon 18 from AGG to AAC. To accomplish this, a single stranded DNA template containing the antibody light chain sequence is prepared from a suitable strain of *E. coli* (e.g., $dut^-$ $ung^-$) in order to obtain a DNA molecule containing a small number of uracils in place of thymidine. Such a DNA template can be obtained by M13 cloning or by in vitro transcription using a SP6 promoter. See, for example, Ausubel et al., eds., CURRENT PROTOCOLS IN MOLECULAR BIOLOGY, John Wiley & Sons, N.Y., 1987. An oligonucleotide complementary to the single stranded DNA, comprising the mutated sequence is synthesized conventionally, annealed to the single-stranded template and the product treated with T4 DNA polymerase and T4 DNA ligase to produce a double-stranded DNA molecule. Transformation of wild type *E. coli* ($dut^+$ $ung^+$) cells with the double-stranded DNA allows recovery of mutated DNA.

Alternatively, an Asn-linked glycosylation site can be introduced into an antibody light chain using an oligonucleotide containing the desired mutation, any amplifying of the oligonucleotide by PCR, and cloning it into the variable regions for the VL chain, or by using RNA from cells that produce the antibody of interest as a template. Also see, Huse, in ANTIBODY ENGINEERING: A PRACTICAL GUIDE, Boerrebaeck, ed., W. H. Freeman & Co., pp 103–120, 1992. Site-directed mutagenesis can be performed, for example, using the TRANSFORMERS™ kit (Clontech, Palo Alto, Calif.) according to the manufacturer's instructions.

Alternatively, a glycosylation site can be introduced by synthesizing an antibody chain with mutually priming oligonucleotides, one such containing the desired mutation. See, for example, Uhlmann, *Gene* 71: 29 (1988); Wosnick et al., *Gene* 60: 115 (1988); Ausubel et al., above, which are incorporated by reference.

Although the description above referred to the introduction of an Asn glycosylation site in position 18 of the light chain of an antibody, it will occur to the skilled artisan that it is possible to introduce Asn-linked glycosylation sites elsewhere in the light chain or in the heavy chain variable region, or in the constant regions.

The presence of a glycosylation site, or the absence of such site in a humanized Ab, where the site was glycosylated in the murine counterpart, may or may not affect the binding affinity or specificity of the antibody. Glycosylation sites therefore can be introduced or removed, by methods described above, but their impact on activity needs to be determined. For reasons discussed above, engineering glycosylation sites in the CH1 or CK regions are preferred.

General Techniques for RNA Isolation, cDNA Synthesis and Amplification

RNA isolation, cDNA synthesis, and amplification can be carried out as follows. Total cell RNA can be prepared from a LL2 hybridoma cell line, using a total of about $10^7$ cells, according to Sambrook et al., (*Molecular Cloning: A Laboratory Manual*, Second ed., Cold Spring Harbor Press, 1989), which is incorporated by reference. First strand cDNA can be reverse transcribed from total RNA conventionally, such as by using the Superscript preamplification system (Gibco/BRL., Gaithersburg, Md.). Briefly, in a reaction volume of 20 μl, 50 ng of random primers can be annealed to 5 μg of RNA in the presence of 2 μl of 10× synthesis buffer [200 mM Tris-HCl (pH 8.4), 500 mM KCl, 25 MM $MgCl_2$, 1 mg/ml BSA], 1 μl of 10 mM dNTP mix, 2 μl of 0.1 M DTT, and 200 units of SuperScript reverse transcriptase. The elongation step is initially allowed to proceed at room temperature for 10 min followed by incubation at 42° C. for 50 min. The reaction can be terminated by heating the reaction mixture at 90° C. for 5 min.

Constructing Antibodies with Engineered Alycosylation Sites in the VL and VH Regions cDNAs encoding the VL and VH regions of the mLL2 mAb have been isolated and recombinantly subcloned into mammalian expression vectors containing the genes encoding kappa and $IgG_1$ constant regions, respectively, of human antibodies. Cotransfection of mammalian cells with these two recombinant DNAs expressed a cLL2 mAb that, like the parent mLL2 mAb, bound avidly to, and was rapidly internalized by B-lymphoma cells.

The CDRs of the VK and VH DNAs have been similarly recombinantly linked to the framework (FR) sequences of the human VK and VH regions, respectively, which are subsequently linked, respectively, to the human kappa and $IgG_1$ constant regions, and expressed hLL2 in mammalian cells.

Once the sequences for the hLL2 VK and VH domains are designed, CDR engrafting can be accomplished by gene synthesis using long synthetic DNA oligonucleotides as templates and amplifying the long oligonucleotides by PCR, using short oligonucleotides as primers. In most cases, the DNA encoding the VK or VH domain will be approximately 350 base pairs (bp) long. By taking advantage of codon degeneracy, a unique restriction site may easily be introduced, without changing the encoded amino acids, at regions close to the middle of the V gene DNA sequence. For example, at DNA nucleotide positions 157–162 (amino acid positions 53 and 54) for the hLL2 VH domain, a unique AvrII site can be introduced while maintaining the originally designed amino acid sequence (FIG. 4B). Two long non-overlapping single-stranded DNA oligonucleotides (~150 bp) upstream and downstream of the AvrII site (see, for example, oligo A and oligo B in Example 3 below) can be generated by automated DNA oligonucleotide synthesizer (Cyclone Plus DNA Synthesizer, Milligen-Biosearch). The yields of full length DNA oligonucleotides such as oligos A and B may be expected to be low. However, they can be amplified by two pairs of flanking oligonucleotides in a PCR reaction. The primers can be designed with the necessary restriction sites to facilitate subsequent subcloning. Primers for oligo A and for oligo B should contain overlapping sequence at the AvrII site so that the resultant PCR product for oligo A and B, respectively, can be joined in-frame at the AvrII site to form a full length DNA sequence (ca 350 bp) encoding the hLL2 VH domain. The ligation of the PCR products for oligo A (restriction-digested with PstI and AvrII) and B (restriction-digested with AvrII and BstEII) at the AvrII site and their subcloning into the PstII/BstEII sites of the staging vector, VHPBS, can be completed in a single three-fragment-ligation step. See for Example 3. The subcloning of the correct sequence into VHpBS can be first analyzed by restriction digestion analysis and subsequently confirmed by sequencing reaction according to Sanger et al., *Proc. Natl. Acad. Sci. USA* 74: 5463 (1977).

The HindIII/BamHI fragment containing the Ig promoter, leader sequence and the hLL2 VH sequence can be excised from the staging vector and subcloned to the corresponding sites in a pSVgpt-based vector, pG1g, which contains the genomic sequence of the human IgG constant region, an Ig enhancer and a gpt selection marker, forming the final expression vector, hLL2pG1g. Similar strategies can be employed for the construction of the hLL2 VK sequence. The restriction site chosen for the ligation of the PCR products for the long oligonucleotides (oligos C and D, see examples below) can be NruI in this case.

The DNA sequence containing the Ig promoter, leader sequence and the hLL2 VK sequence can be excised from the staging vector VKpBR by treatment with BamH1/HindIII, and can be subcloned into the corresponding sites of a pSVhyg-based vector, pKh, which contains the genomic sequence of human kappa chain constant regions, a hygromycin selection marker, an Ig and a kappa enhancer, to form the final expression vector, hLL2pKh.

Humanization sometimes results in a reduction or even loss of antibody affinity. Therefore, additional modification might be required in order to restore the original affinity. See, for example, Tempest et al., *Bio/Technology* 9: 266 (1991); Verhoeyen et al., *Science* 239: 1534 (1988), which are incorporated by reference. Knowing that cLL2 exhibits a binding affinity comparable to that of its murine counterpart (see Example 5 below), defective designs, if any, in the original version of hLL2 can be identified by mixing and matching the light and heavy chains of cLL2 to those of the humanized version. SDS-PAGE analysis of the different mix-and-match humanized chimeric LL2 under non-reducing (the disulfide L-H chain connections remain intact) and reducing conditions (the chains separate) permits analyses of the relationships of the different types of light and heavy chains on the properties of the molecule. For example, migration as multiple bands or as a higher apparent molecular size can be due to the presence of a glycan group at the N-linked glycosylation site found in the FR1 region of the murine VK domain of LL2. A discrete band migrating at about 25 kDa is the expected molecular size for a non-glycosylated light chain.

In general, to prepare cLL2 mAb, VH and VK chains of mLL2 can be obtained by PCR cloning using DNA products and primers. Orlandi et al., infra, and Leung et al., infra. The VK PCR primers may be subcloned into a pBR327-based staging vector (VKpBR) as described above. The VH PCR products may be subcloned into a similar pBluescript-based staging vector (VHpBS) as described above. The fragments containing the VK and VH sequences, along with the promoter and signal peptide sequences, can be excised from the staging vectors using HindIII and BamHI restriction endonucleases. The VK fragments which are about 600 bp can be subcloned into a mammalian expression vector, pKh for example, by conventional methods. pKh is a pSVhyg-based expression vector containing the genomic sequence of the human kappa constant region, an Ig enhancer, a kappa enhancer and the hygromycin-resistant gene. Similarly, the about 800 bp VH fragments can be subcloned into pG1g, a pSVgpt-based expression vector carrying the genomic sequence of the human IgG1 constant region, an Ig enhancer and the xanthine-guanine phosphoribosyl transferase (gpt) gene. The two plasmids may be transfected into mammalian expression cells, such as Sp2/0-Ag14 cells, by electroporation and selected for hygromycin resistance. Colonies surviving selection are expanded, and supernatant fluids monitored for production of cLL2 mAb by an ELISA method. A transfection efficiency of about $1-10\times10^6$ cells is desirable. An antibody expression level of between 0.10 and 2.5 µg/ml can be expected with this system.

General Techniques for RNA Isolation, cDNA Synthesis and Amplification

RNA isolation, cDNA synthesis, and amplification can be carried out as follows. Total cell RNA can be prepared from a LL2 hybridoma cell line, using a total of about $10^7$ cells, according to Sambrook et al., (*Molecular Cloning: A Laboratory Manual*, Second ed., Cold Spring Harbor Press, 1989), which is incorporated by reference. First strand cDNA can be reverse transcribed from total RNA conventionally, such as by using the Superscript preamplification system (Gibco/BRL., Gaithersburg, Md.). Briefly, in a reaction volume of 20 µl, 50 ng of random primers can be annealed to 5 µg of RNAs in the presence of 2 µl of 10× synthesis buffer [200 mM Tris-HCl (pH 8.4), 500 mM KCl, 25 mM $MgCl_2$, 1 mg/ml BSA], 1 µl of 10 mM dNTP mix, 2 µl of 0.1 M DTT, and 200 units of SuperScript reverse transcriptase. The elongation step is initially allowed to proceed at room temperature for 10 min followed by incubation at 42° C. for 50 min. The reaction can be terminated by heating the reaction mixture at 90° C. for 5 min.

Amplification of VH and VK sequences.

The VK and VH sequences for cLL2 or hLL2 can amplified by PCR as described by Orlandi et al., (*Proc. Natl. Acad. Sci., USA*, 86: 3833 (1989)) which is incorporated by reference. VK sequences may be amplified using the primers CK3BH and VK5-3 (Leung et al., *BioTechniques*, 15: 286 (1993), which is incorporated by reference), while VH sequences can be amplified using the primer CHLB which anneals to the CH1 region of murine 1gG, and VHIBACK (Orlandi et al., 1989 above). The PCR reaction mixtures containing 10 µl of the first strand cDNA product, 9 µl of 10× PCR buffer [500 mM KCl, 100 mM Tris-HCl (pH 8.3), 15 mM MgCl2, and 0.01% (w/v) gelatin] (Perkin Elmer Cetus, Norwalk, Conn.), can be subjected to 30 cycles of PCR. Each PCR cycle preferably consists of denaturation at 94° C. for 1 min, annealing at 50° C. for 1.5 min, and polymerization at 72° C. for 1.5 min. Amplified VK and VH fragments can be purified on 2% agarose (BioRad, Richmond, Calif.). See Example 3 for a method for the synthesis of an oligo A (149-mer) and an oligo B (140-mer) on an automated Cyclone Plus DNA synthesizer (Milligan-Biosearch).

PCR products for VK can be subcloned into a staging vector, such as a pBR327-based staging vector VKPBR that contains an Ig promoter, a signal peptide sequence and convenient restriction sites to facilitate in-frame ligation of the VK PCR products. PCR products for VH can be subcloned into a similar staging vector, such as the pBluescript-based VHpBS. Individual clones containing the respective PCR products may be sequenced by, for example, the method of Sanger et al., *Proc. Natl. Acad. Sci., USA*, 74: 5463 (1977) which is incorporated by reference.

Furthermore, it was found that the presence of glycosylation sites, and therefore of appended carbohydrate (CHO) moieties causes efficient and superior conjugation of drugs and chelates. This is especially true when antibody fragments devoid of CH2-appended CHO are being utilized.

The DNA sequences described herein include all alleles, mutants and variants thereof, whether occurring naturally or experimentally created.

Production of Antibodies with Mutated CH1 and CK Regions

CH1 and CK DNA sequences can be isolated, the protein sequence modeled, and the DNA mutated by methodologies similar to these described for the VK and VH sequences. Once the CH1 or CK nucleotide sequence has been excised from a light or heavy chain clone, and a glycosylation site inserted via mutagenesis, the mutated CH1 or CK sequence can be re-inserted into the corresponding heavy or light chain vector. In the case of a CH1 mutant, it can be coexpressed with a kappa chain expression vector, such as hLL2pKh, into an appropriate cell, e.g., myeloma Sp2/0-Ag14, and colonies can be selected for hygromycin resistance. The supernatant fluids can be monitored for production of cLL2, hLL2, or LL2 engineered with glycosylation sites in the non Fc constant regions according to the invention by, for example, an ELISA assay, as described below.

Transfection, and assay for antibody secreting clones by ELISA, can be carried out as follows. About 10 µg of hLL2pKh (light chain expression vector) and 20 µg of hLL2pG1g (heavy chain expression vector) can be used for the transfection of $5\times10^6$ SP2/0 myeloma cells by electroporation (BioRad, Richmond, Calif.) according to Co et al., *J. Immunol.*, 148: 1149 (1992) which is incorporated by reference. Following transfection, cells may be grown in 96-well microtiter plates in complete HSFM medium (GIBCO, Gaithersburg, Md.) at 37° C., 5% $CO_2$. The selection process can be initiated after two days by the addition of hygromycin selection medium (Calbiochem, San Diego, Calif.) at a final concentration of 500 µg/ml of hygromycin. Colonies typically emerge 2–3 weeks post-electroporation. The cultures can then be expanded for further analysis.

The level of expression of an Ig gene containing clone could be enhanced by amplifying the copy number. This is typically done by selection for a selectable marker linked to the gene of interest, here the Ig gene. One skilled in the art would be familiar with the use of such selection. Often the selective marker is the dihydrofolate reductase gene (dhfr). Typically, a clone that appears to contain an amplified copy number of the gene is identified by its expression and amplification is confirmed by nucleic acid hybridization experiments. Multiple rounds of selection assay and confirmation by hybridization are typically undertaken.

Transfectoma clones that are positive for the secretion of cLL2, hLL2, or LL2 engineered with glycosylation sites in the non Fc constant regions according to the invention can be identified by ELISA assay. Briefly, supernatant samples (100 µl) from transfectoma cultures are added in triplicate to ELISA microtiter plates precoated with goat anti-human (GAH)-IgG, F(ab')$_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch, West Grove, Pa.) are added to the wells, (100 µl of antibody stock diluted×$10^4$, supplemented with the unconjugated antibody to a final concentration of 1.0 µg/ml). Following an incubation of 1 h, the plates are washed, typically three times. A reaction solution, [100 µl, containing 167 µg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 µl of 4 N HCl solution into each well before measuring absorbance at 490 nm in an automated ELISA reader (Bio-Tek instruments, Winooski, Vt.). Bound antibodies are than determined relative to an irrelevant chimeric antibody standard (obtainable from Scotgen, Ltd., Edinburgh, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 micron membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 $\mu$l of 3 M Tris (pH 8.6), and protein concentrations determined from the absorbencies at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

Comparative binding affinities of the antibodies thus isolated may be determined by direct radioimmunoassay. An cLL2, hLL2, or LL2 engineered with glycosylation sites in the non Fc constant regions according to the invention can be used. Antibodies can be labeled with $^{131}$I, or $^{125}$I using the chloramine T method (see, for example, Greenwood et al., *Biochem. J.*, 89: 123 (1963) which is incorporated by reference). The specific activity of the iodinated antibody is typically adjusted to about 10 $\mu$Ci/$\mu$g. Unlabeled and labeled antibodies are diluted to the appropriate concentrations using reaction medium (HSFM supplemented with 1% horse serum and 100 $\mu$g/ml gentamicin). The appropriate concentrations of both labeled and unlabeled antibodies are added together to the reaction tubes in a total volume of 100 $\mu$l. A culture of Raji cells is sampled and the cell concentration determined. The culture is centrifuged and the collected cells washed once in reaction medium followed by resuspension in reaction medium to a final concentration of about $10^7$ cells/ml. All procedures are carried out in the cold at 4° C. The cell suspension, 100 $\mu$l, is added to the reaction tubes. The reaction is carried out at 4° C. for 2 h with periodic gentle shaking of the reaction tubes to resuspend the cells. Following the reaction period, 5 ml of wash buffer (PBS containing 1% BSA) is added to each tube. The suspension is centrifuged and the cell pellet washed a second time with another 5 ml of wash buffer. Following centrifugation, the amount of remaining radioactivity remaining in the cell pellet is determined in a gamma counter (Minaxi, Packard Instruments, Sterling, Va.).

The antigen-binding property of the antibodies of the invention can be evaluated by competition binding with labeled mLL2 for an LL2 anti-idiotype antibody (WN).

The Raji cell surface antigen binding affinities of mix-and-match and fully humanized antibodies can be compared to that of cLL2 using various concentrations of mLL2 F(ab')$_2$ fragments devoid of the Fc portion as competitors, as evaluated by flow cytometry assay. Residual surface-bound LL2 antibodies carrying the human Fc portions (cLL2 and mix-and-match LL2) can be detected by a FITC-labeled anti-human Fc specific antibody in a flow cytometry assay. Where mix-and-match LL2 antibodies exhibit antigen-binding affinities similar to that of cLL2, it can be concluded that the original designs for the humanization of both the light and heavy chains retain the mLL2 immunoreactivity.

The internalization of cLL2, hLL2, or LL2 engineered with glycosylation sites in the non Fc constant regions according to the invention into target cells can be followed by fluorescence labeling, essentially according to the procedure of Pirker et al., *J. Clin. Invest.*, 76: 1261 (1985), which is incorporated by reference. Cultured Raji cells are centrifuged and the cells resuspended in fresh medium to a concentration of about 5×10$^6$ cells/ml. To each well of a 96-well microtiter plate, 100 $\mu$l of the cell suspension is added. The antibodies, 40 $\mu$g/ml, in a volume of 100 $\mu$l are added to the reaction wells at timed intervals so as to terminate all reactions simultaneously. The plate is incubated at 37° C. in a CO$_2$ cell culture incubator. Unbound antibodies are removed by washing the cells three times with cold 1% FCS/PBS at the end of the incubation. The cells are then treated with 1 ml of Formaid-Fresh [10% formalin solution (Fisher, Fair Lawn, N.J.)] for 15 min at 4° C. After washing, antibodies present either on the cell surface or inside the cells are detected by treatment with FITC-labeled goat anti-mouse antibody (Tago, Burlingame, Calif.), or FITC-labeled goat anti-human antibody (Jackson ImmunoResearch, West Grove, Pa.), depending on whether the antibody being assayed for is murine, chimeric, or humanized, respectively. Fluorescence distributions are evaluated using a BH-2 fluorescence microscope (Olympus, Lake Success, N.Y.).

The rate of antibody internalization can be determined according to Opresko et al., (*J. Biol. Chem.*, 262: 4116 (1987)), using radio-iodinated antibody as tracer. Briefly, radiolabelled antibodies (1×10$^4$ cpm) are incubated with the Raji cells (1×10$^6$ cells/ml) at 4° C. for 2 h in 0.5 ml of DMEM medium containing 1% human serum. Following the reaction interval, non-specifically bound antibodies are removed by washing three times with 0.5 ml of DMEM medium. To each of the reaction tubes 0.5 ml of DMEM medium is added and the suspension incubated at 37° C. for the determination of internalization. At timed intervals, triplicates of cells are removed and chilled immediately in an ice bath to stop further internalization. Cells are centrifuged at 1000×g for 5 min at 4° C. The supernatant is removed and counted for radioactivity. The surface-bound radioactivity is removed by treatment with 1 ml 0.1 M acetate/0.1 M glycine buffer at pH 3.0 for 8 min. in the cold. Radioactivity removed by the acid treatment, and that remaining associated with the cells, are determined. The ratio of the CPM$_{internalization}$/CPM$_{surface}$ is plotted versus time to determine the rate of internalization from the slope.

The representative embodiments described below are simply used to illustrate the invention. Those skilled in these arts will recognize that variations of the present materials fall within the broad generic scope of the claimed invention. The contents of all references mentioned herein are incorporated by reference.

EXAMPLE 1

Figure 2B:
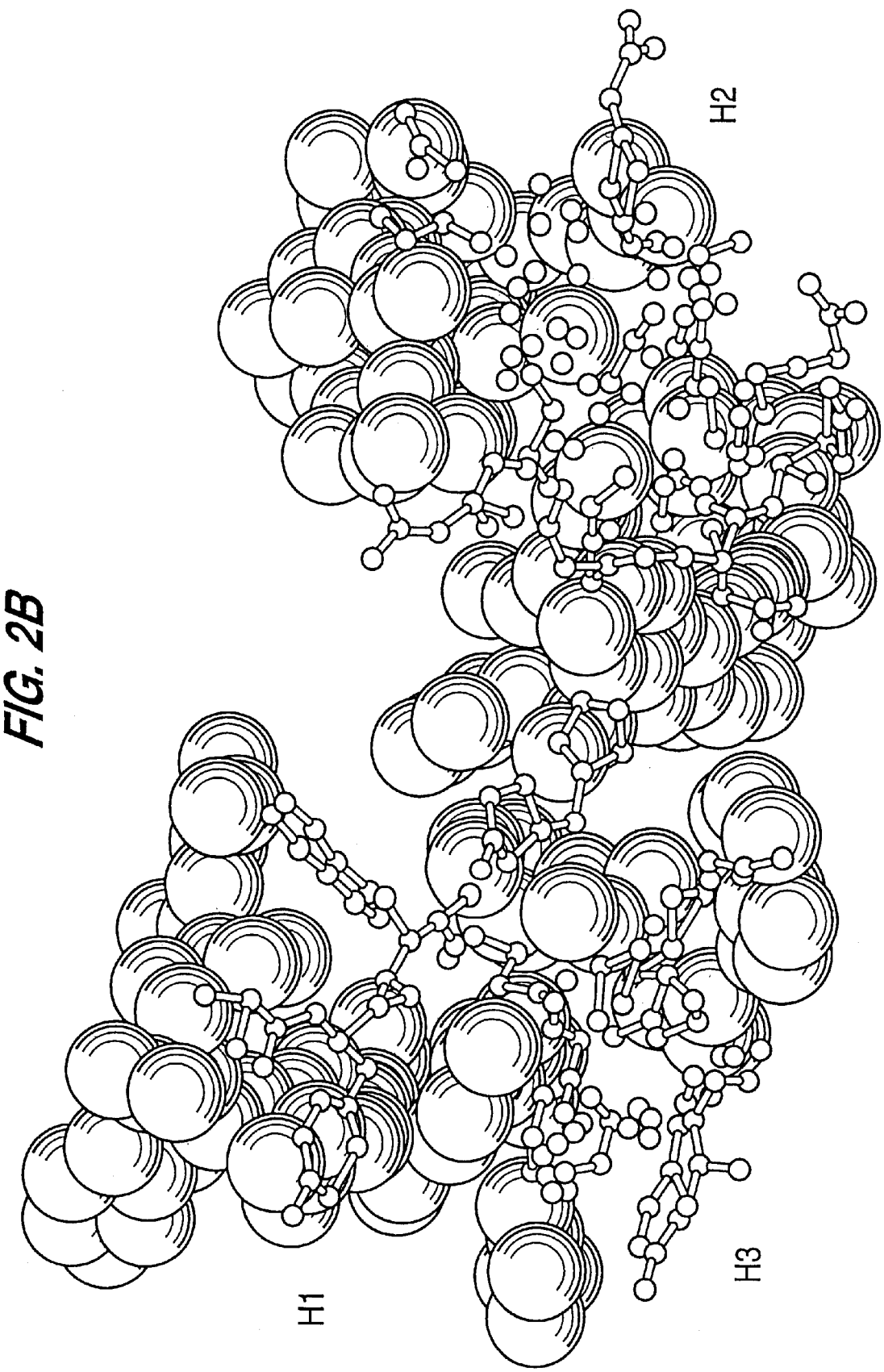

Choice of Human Frameworks and Sequence Design for the Humanization of LL2 Monoclonal Antibody By comparing the murine variable (V) region framework (FR) sequences of LL2 to that of human antibodies in the Kabat data base (Kabat et al., *Sequences of Proteins of Immunological Interest*, 5th ed., U.S. Department of Health and Human Services, U.S. Government Printing Office, Washington, D.C.), which is incorporated by reference, the human REI (FIG. 1A,) and EU (FIG. 1B) sequences were found to exhibit the highest degree of sequence homology to the FRs of VK and VH domains of LL2, respectively. Therefore, the REI and EU FRs were selected as the human frameworks onto which the CDRs for LL2 VK and VH were grafted, respectively. The FR4 sequence of NEWM, however, rather than that of EU, was used to replace the EU FR4 sequence for the humanization of LL2 heavy chain. Based on the results of computer modeling studies (FIGS. 2A and 2B), murine FR residues having potential CDR contacts, which might affect the affinity and specificity of the resultant antibody, were retained in the design of the humanized FR sequences (FIG. 1).

Two versions of humanized heavy chain were constructed. In the first version (hLL2-1), the glutamine (Q) at amino acid position 5 (Kabat numbering) was introduced to include a PstI restriction site to facilitate its subcloning into the staging vector (FIG. 3). This murine residue was converted, by oligo-directed mutagenesis, to the human EU residue valine (V) in hLL2-2. It should be noted that in the original murine kappa chain variable sequence, a potential N-linked glycosylation site was identified at positions 18–20 and was used for carbohydrate addition. This glycosylation site was not included in the REI FR sequence used for LL2 light chain humanization.

EXAMPLE 2

PCR Cloning and Sequence Elucidation for LL2 Heavy and Light Chain Variable Regions The variable regions for both heavy (VH) and light (VK) chains of mLL2 (IgG2a) were obtained by PCR cloning using DNA primers as described in general above and in greater detail in Example 3, below. As PCR is prone to mutations, the variable region sequence of multiple individual clones for either the heavy or light chains was determined for six clones and confirmed to be identical prior to use for the construction of the chimeric antibody.

Figure 3A:
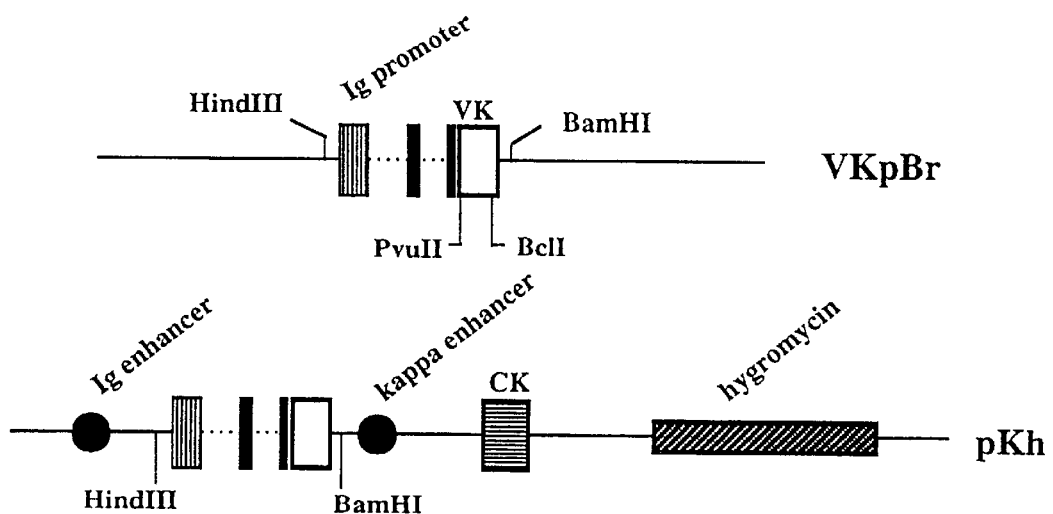
Figure 3B:
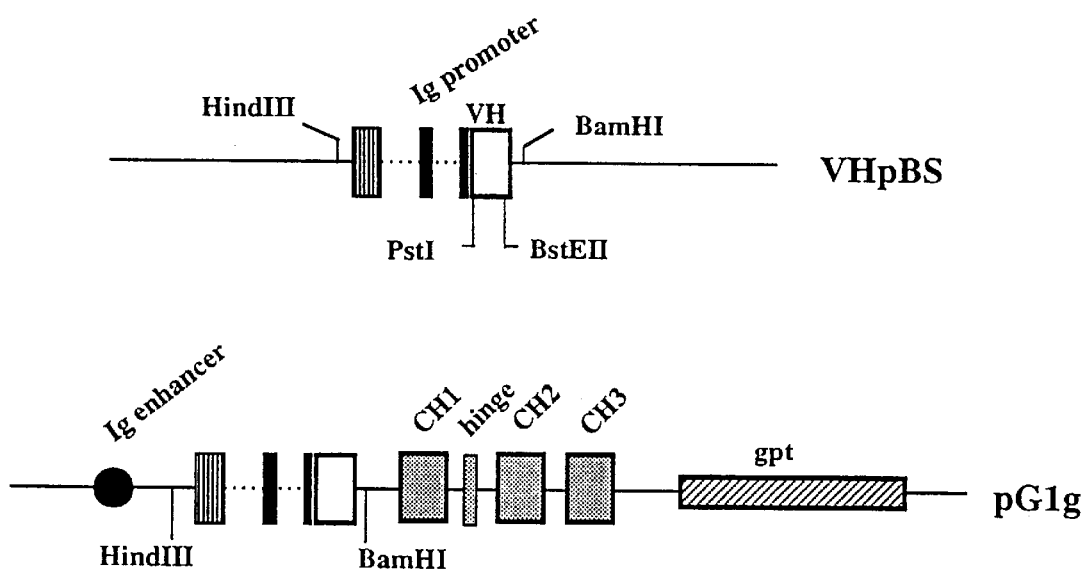

The PCR products for VK were subcloned into a pBR327-based staging vector, VKpBR, which contained an Ig promoter, a signal peptide sequence and convenient restriction sites to facilitate in-frame ligation of the VK PCR products (FIG. 3A). The PCR products for VH were subcloned into a similar pBluescript-based staging vector, VHpBS (FIG. 3B).

As noted above, at least six individual clones containing the respective PCR products were sequenced according to the method of Sanger et al., 1977, above. All were shown to bear identical sequences and their respective sequences were elucidated, as shown in FIG. 4A for LL2 VK and in FIG. 4B for LL2 VH. No defective mutations were identified within the sequences encoding the VK and VH regions. Comparison of the PCR-amplified variable region sequences of LL2 with the Kabat database (Kabat et al., above) suggested that the VK and VH sequences of LL2 belong to subgroup 5 and 2B, respectively. Important residues such as Cys for intradomain disulfide linkage were retained at appropriate positions.

In the FRI framework region of VK, an N-linked carbohydrate attachment site, Asn-Val-Thr, was identified at position 18–20 (FIG. 4A), suggesting that the VK of LL2 might be glycosylated. As will be detailed below, SDS-PAGE analysis under reducing conditions demonstrated that this Asn glycosylation site is indeed utilized for carbohydrate addition. The presence of the glycosylation site in the variable region does not, however, appear to affect the immunoreactivity of the antibody. A comparison of the immunoreactivity of mLL2 with that of cLL2 in a competitive RIA showed that the two antibodies have nearly identical activities.

EXAMPLE 3

PCR/Gene Synthesis of the Humanized V Genes

The designed sequence for the hLL2 VH domain, the construction of the hLL2 VH domain by long oligonucle-otides and PCR, and the staging vector VHpBS containing the hLL2 VH domain are summarized in the sketch shown in FIG. 6.

For the construction of the hLL2 VH domain, oligo A (149-mer) and oligo B (140-mer) were synthesized on an automated CYCLONE PLUS™ DNA synthesizer (Milligen Bioresearch).

Oligo A represents the minus strand of the hLL2 VH domain complementary to nucleotides 24 to 172 (SEQ ID NO:22):5'-TAT AAT CAT TCC TAG GAT TAA TGT ATC CAA TCC ATT CCA GAC CCT GTC CAG GTG CCT GCC TGA CCC AGT GCA GCC AGT AGC TAG TAA AGG TGT AGC CAG AAG CCT TGC AGG AGA CCT TCA CTG ATG ACC CAG GTT TCT TGA CTT CAG CC-3'

Oligo B represents the minus strand of the hLL2 VH domain complementary to nt 180 to 320 (SEQ ID NO:23) :5'-CCC CAG TAG AAC GTA GTA ATA TCC CTT CTT GCA CAA AAA TAA AAT GCC GTG TCC TCA GAC CTC AGG CTG CTC AGC TCC ATG TAG GCT GTA TTG GTG GAT TCG TCT GCA GTT ATT GTG GCC TTG TCC TTG AAG TTC TGA TT-3'

Oligos A and B were cleaved from the support and deprotected by treatment with concentrated ammonium hydroxide. After the samples were vacuum-dried (SpeedVac, Savant, Farmingdale, N.Y.) and resuspended in 100 μl of water, incomplete oligomers (less than 100-mer) were removed by centrifugation through a CHROMOSPIN-100™ column (Clonetech, Palo Alto, Calif.) before the DNA oligomers were amplified by PCR. All flanking primers for the separate amplifications and PCR cloning of oligos A and B were purified by SDS-PAGE essentially according to the methods of Sambrook et al., 1989, above. From the CHROMASPIN-purified oligo A, 1 μl of sample stock was PCR-amplified in a reaction volume of 100 μl by adding 5 μl of 5 μM of oligo (SEQ ID NO:24): 5'-CCA GCT GCA GCA ATC AGG GGC TGA AGT CAA GAA ACC TG-3' and of oligo (SEQ ID NO:25): 5'-AAG TGG ATC CTA TAA TCA TTC CTA GGA TTA ATG-3' in the presence of 10 μl of 10× PCR Buffer (500 mM KCl, 100 mM Tris-HCL buffer, pH 8.3, 15 mM MgCl₂) and 5 units of AMPLITAQ™ DNA polymerase (Perkin Elmer Cetus, Norwalk, Conn.). This reaction mixture was subjected to 30 cycles of PCR reaction consisting of denaturation at 94° C. for 1 minute, annealing at 50° C. for 1.5 minutes, and polymerization at 72° C. for 1.5 minutes.

Oligo B was PCR-amplified by the primer pairs: 5'-TAA TCC TAG GAA TGA TTA TAC TGA GTA CAA TCA GAA CTT CAA GGA CCA G-3' (SEQ ID NO:26) and: 5'-GGA GAC GGT GAC CGT GGT GCC TTG GCC CCA GTA GAA CGT AGT AA-3' (SEQ ID NO:27) under similar conditions.

Double-stranded PCR-amplified products for oligos A and B were gel-purified, restriction-digested with PstI/AvrII (PCR product of oligo A) and BstEII/AvrII (PCR product of oligo B), and subcloned into the complementary PstI/BstEII sites of the heavy chain staging vector, VHpBS. The humanized VH sequence was subcloned into the pG1g vector, resulting in the final human IgG1 heavy chain expression vector, hLL2pG1g.

For constructing the full length DNA of the humanized VK sequence, oligo E (150-mer) and oligo F (121-mer) were synthesized as described above. oligo E comprises (SEQ ID NO:28): 5'-CCT AGT GGA TGC CCA GTA GAT CAG CAG TTT AGG TGC TTT CCC TGG TTT CTG GTG GTA CCA GGC CAA GTA GTT CTT GTG ATT TGC ACT GTA TAA AAC ACT TTG ACT GGA CTT ACA GCT CAT AGT GAC CCT ATC TCC AAC AGA TGC GCT CAG-3'. It represents the minus strand of the humanized VK domain complementary to nt 31 to 180, and this sequence was PCR-amplified by oligo (SEQ ID NO:29): 5'-GAC AAG CTT CAG CTG ACC CAG TCT CCA TCA TCT CTG AGC GCA TCT GTT GGA G-3' and oligo (SEQ ID NO:30): 5'-AGA GAA TCG CGA AGG GAC ACC AGA TTC CCT AGT GGA TGC CCA GTA-3'.

The Oligo F sequence is 5'-CCA GCT TGG TCC CTC CAC CGA ACG TCC ACG AGG AGA GGT ATT GGT GAC AAT AAT ATG TTG CAA TGT CTT CTG GTT GAA GAG AGC TGA TGG TGA AAG TAA AAT CTG TCC CAG ATC CGC TGC C-3'. It represents the minus strand of the humanized LL2 VK domain complementary to nt 208 to 328. It was PCR amplified by oligo (SEQ ID NO:32): 5'-GAC AAG CTT TCG CGA TTC TCT GGC AGC GGA TCT GGG ACA G-3' and oligo (SEQ ID NO:33): 5'-GAC CGG CAG ATC TGC ACC TTG GTC CCT CCA CCG-3'.

Gel-purified PCR products for oligos E and F were restriction-digested with PvuII/NruI and NruI/BglIII, respectively. The two PCR fragments E and F were then joined at the NruI site and ligated to the complementary PvuI/BclI sites of the light chain staging vector, VKpBR. The humanized VK sequence was subcloned into vector pKh to form the final human kappa chain expression vector, hLL2pKh.

To express the humanized antibodies, about 10 μg of linearized hLL2pKh and 20 μg of linearized hLL2pG1g were used to transfect 5×10⁶ SP2/0 cells by electroporation. The transfectomas were selected with hygromycin at 500 μg/ml and secreted antibody was purified on a 1×3 cm column of protein A. After concentrating the purified antibody by Centricon 30 centrifugation, antibody concentration was determined by ELISA. The final concentration of the antibody was adjusted to 1 mg/ml in PBS buffer containing 0.01% (w/v) sodium azide as a preservative.

FIG. 1 compares the amino acid sequence between murine and humanized LL2 VK domains (FIG. 1A, SEQ ID NOS 2, 6, & 20)) and between murine and humanized LL2 VH domains (FIG. 1B, (SEQ ID NOS 4, 21, & 8). In the VK chain, human REI framework sequences were used for all FRs. In the VH chain, human EU framework sequences were used for FR 1–3, and NEWM sequences were used for FR-4. Only human FR sequences that are different from that of the mouse are shown. Asterisks indicate murine FR sequences that are different from that of the human FR at corresponding positions. Murine residues at these positions were retained in the humanized structure. CDRs are boxed.

In FIG. 4A (SEQ ID NOS 1 & 2) there are shown the double stranded DNA and corresponding amino acid sequences (shown by single letter code) of the murine LL2 VK domain. CDR 1–3 amino acid sequences are boxed. The corresponding display for VH is shown in FIG. 4B (SEQ ID NOS 3 & 4).

In FIG. 5A (SEQ ID NOS 5 & 6) and FIG. 5B (SEQ ID NOS 7 & 8)there are shown double-stranded DNA sequences and amino acid sequences of humanized LL2 VK and LL2 VH, respectively. Amino acid sequences are shown by the single-letter code, and CDR amino acid sequences are boxed.

EXAMPLE 4

Construction, Expression and Purification of Chimeric LL2 Antibodies

The fragments containing the VK and VH sequences of LL2, together with the promoter and signal peptide sequences, were excised from LL2VKpBR and LL2VHpBS, respectively, by double restriction digestion with HindIII and BamHI. The about 600 bp VK fragments were then subcloned into the HindIII/BamHI site of a mammalian expression vector, pKh (FIG. 3A). pKh is a pSVhyg-based expression vector containing the genomic sequence of the human kappa constant region, an Ig enhancer, a kappa enhancer and the hygromycin-resistant gene. Similarly, the ca. 800 bp VH fragments were subcloned into the corresponding HindIII/BamHI site of pG1g (FIG. 3B), a pSVgpt-based expression vector carrying the genomic sequence of the human IgG1 constant region, an Ig enhancer and the xanthine-guanine phosphoribosyltransferase (gpt) gene. The final expression vectors are designated as LL2pKh and LL2pG1g, respectively.

The two plasmids were co-transfected into Sp2/0-Ag14 cells by electroporation and selected for hygromycin resistance. Supernatant from colonies surviving selection were monitored for chimeric antibody secretion by ELISA assay (see above). The transfection efficiency was approximately 1–10×10⁶ cells. The antibody expression level, in a terminal culture, was found to vary in the range between <0.10 and 2.5 μg/ml.

Protein A-purified mLL2 and cLL2 were analyzed by SDS-PAGE under reducing and non-reducing conditions. The light chains of both mLL2 and cLL2 showed a higher than expected apparent molecular weight. As the human kappa constant region of cLL2 is known to contain no potential glycosylation site, it can be inferred that the potential glycosylation site identified in the FR1 region of LL2 VK domain was utilized. Different versions of hLL2 and cLL2 antibodies were analyzed by SDS-PAGE under reducing and non-reducing conditions. One hLL2 version was hLL2-1 (with seven murine FR residues in the VH domain). Another hLL2 version was hLL2-2 with 6 murine FR residues in the VH domain. The humanized light chains migrated more rapidly and the bands were more discrete bands when compared to the chimeric light chains.

Mix-and-match, cLL2 and hLL2 antibodies were analyzed by SDS-PAGE, under reducing and non-reducing conditions. The mix-and-match versions analyzed were the (hL/cH)LL2, the (cL/hH)LL2-1, and the (cL/hH)LL-2. (cL/hH)LL-1 and (cL/hH)LL-2 contain 7 and 6 murine residues in the FR regions of the heavy chain, respectively. The migration observed for the (hL/cH)LL2 suggested that the humanized LL2 light chain did not undergo glycosylation.

EXAMPLE 5

Binding of cLL2 Antibody to Raji Cell Surface Antigens

Figure 7:
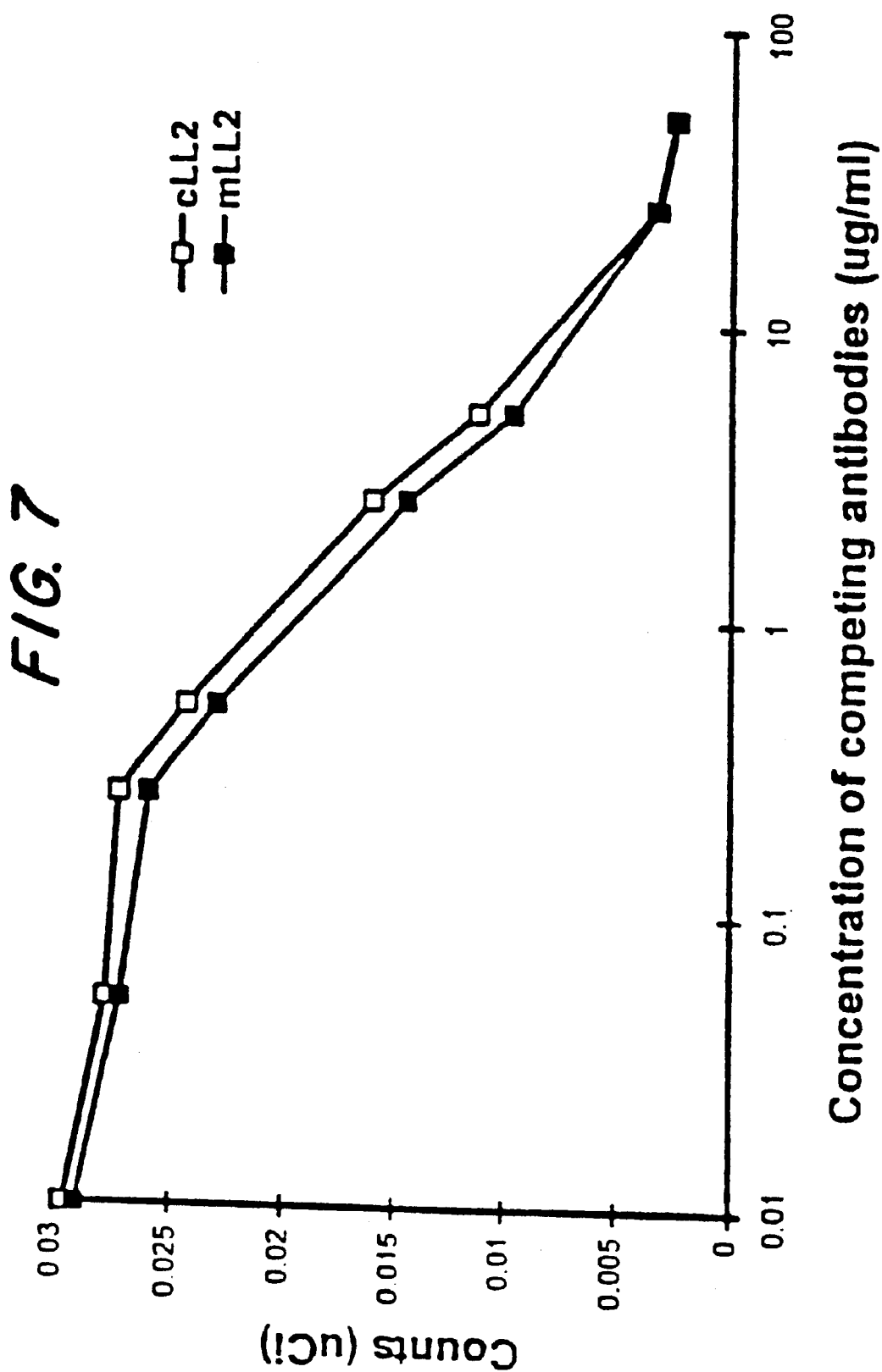
FIG. 7 shows the results of a comparative Raji cell competitive antibody binding assay involving mLL2 and cLL2 antibodies competing for binding to cells against tracer radiolabeled mLL2.

A competition cell binding assay was carried out to assess the immunoreactivity of cLL2 relative to the parent mLL2. Using ¹³¹I-labeled mLL2 (0.025 μg/ml) as a probe, Raji cells were incubated with the antibodies and the relative binding to the cells determined from the amount of cell-bound labeled mLL2 (see above). As shown by the competition assays described in FIG. 7, both mLL2 and cLL2 antibodies exhibited similar binding activities.

The results were confirmed by a second competition assay based on flow cytometry. Briefly, using Raji cells as before and varying the concentration of one antibody relative to other, as before, the amount of bound mLL2 or cLL2 was determined with FITC-labeled anti-mouse Fc or anti-human Fc antibodies followed by analysis using flow cytometry.

EXAMPLE 6

Binding of hLL2 Antibodies to Raji Cells

In experiments similar to those of Example 5, the antigen binding affinities of the three different combinations of mix-and-match or humanized LL2 were compared with that of cLL2 in the flow cytometry assay.

Figure 8B:
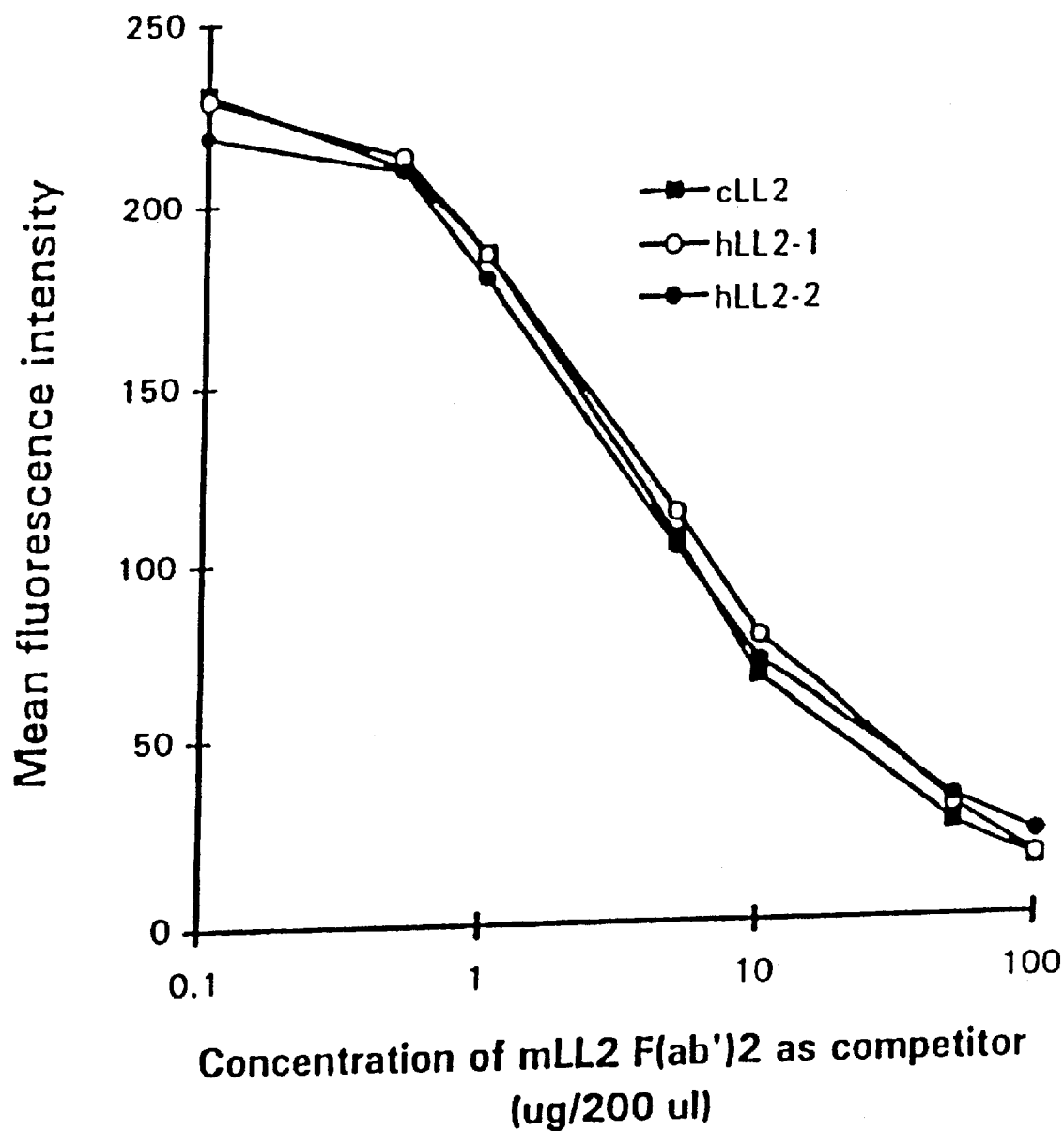
FIG. 8 shows the results of a comparative Raji cell competitive antibody binding assay in which mixed humanized/chimeric LL2s were compared to cLL2 (FIG. 8A), and two versions of hLL2 compared to cLL2 (FIG. 8B).

Briefly, 1 µg of cLL2, mix-and-match LL2, hLL2-1 or hLL2-2 antibodies were incubated with $10^8$ Raji cells in the presence of varying concentrations of mLL2 F(ab')$_2$ fragments (as competitor) in a final volume of 100 µl of PBS buffer supplemented with 1% FCS and 0.01% sodium azide. The mixture was incubated for 30 minutes at 4° C., and washed three times with PBS to remove unbound antibodies. By taking advantage of the presence of human Fc portions in the antibodies, the binding levels of the antibodies were assessed by adding a 20× diluted FITC-labeled goat anti-human IgG1, Fc fragment-specific antibodies (Jackson ImmunoResearch, West Grove, Pa.). The cells were washed three times with PBS, and fluorescence intensities measured by a FACSCAN fluorescence activated cell sorter (Becton-Dickinson, Bedford, Mass.). The results are shown in FIG. 8A. Using the same methods, cLL2 was compared to two versions of hLL2 (FIG. 8B).

The results shown in FIGS. 8A and B demonstrate that the immunoreactivity of cLL2 is similar or identical to that of humanized or mix-and-match antibodies. Taken together with the comparison of cLL2 with mLL2 (FIG. 7), the authenticity of the sequences for chimeric and humanized VK and VH obtained is established, and the functionality of cLL2 and hLL2 confirmed.

EXAMPLE 7

Internalization of mLL2 and cLL2 by Raji Cells

One of the unique characteristics of the LL2 antibody is its rapid internalization upon binding to Raji cells (Shih et al., 1994 above). Murine LL2 after internalization is likely to be rapidly transferred to the Golgi apparatus and from there to the lysosome, the organelle responsible for the degradation of a wide variety of biochemicals (Keisari et al., *Immunochem.*, 10: 565 (1973)).

Rates of antibody internalization were determined according to Opresko et al., 1987 above. The ratio of $CPM_{intracellular}/CPM_{surface}$ was determined as a function of time.

Rates of LL2 antibody internalization were determined by incubating radiolabelled LL2 antibody (1–10$^6$cpm) with 0.5×10$^6$ Raji cells in 0.5 ml of DMEM buffer containing 1% human serum for 2 hrs. at 4° C. Excess human serum was included to saturate Raji cell surface Fc receptors in order to exclude or minimize non-antigen-specific internalization mediated through the Fc receptors. Unbound radiolabelled LL2 antibodies were removed from the cells by washing three times with 0.5 ml portions of DMEM at 4° C. Cells were then incubated at 37° C., and, at timed intervals, aliquots of the cell suspension were transferred to ice in order to stop internalization. The cells in these aliquots were isolated by centrifugation at 1,000×g for 5 mins. at 4° C., and surface bound radiolabelled LL2 stripped off cells with 1 ml of 0.1 M glycine acetate buffer, pH 3, for 8 mins. at 4° C. Radioactivity thus obtained (CPM surface) and radioactivity remaining in the cells (CPM intracellular) were determined. Rates of internalization were calculated from the slope of the plot of intracellular:surface radioactivity ratios as a function of time.

Figure 9:
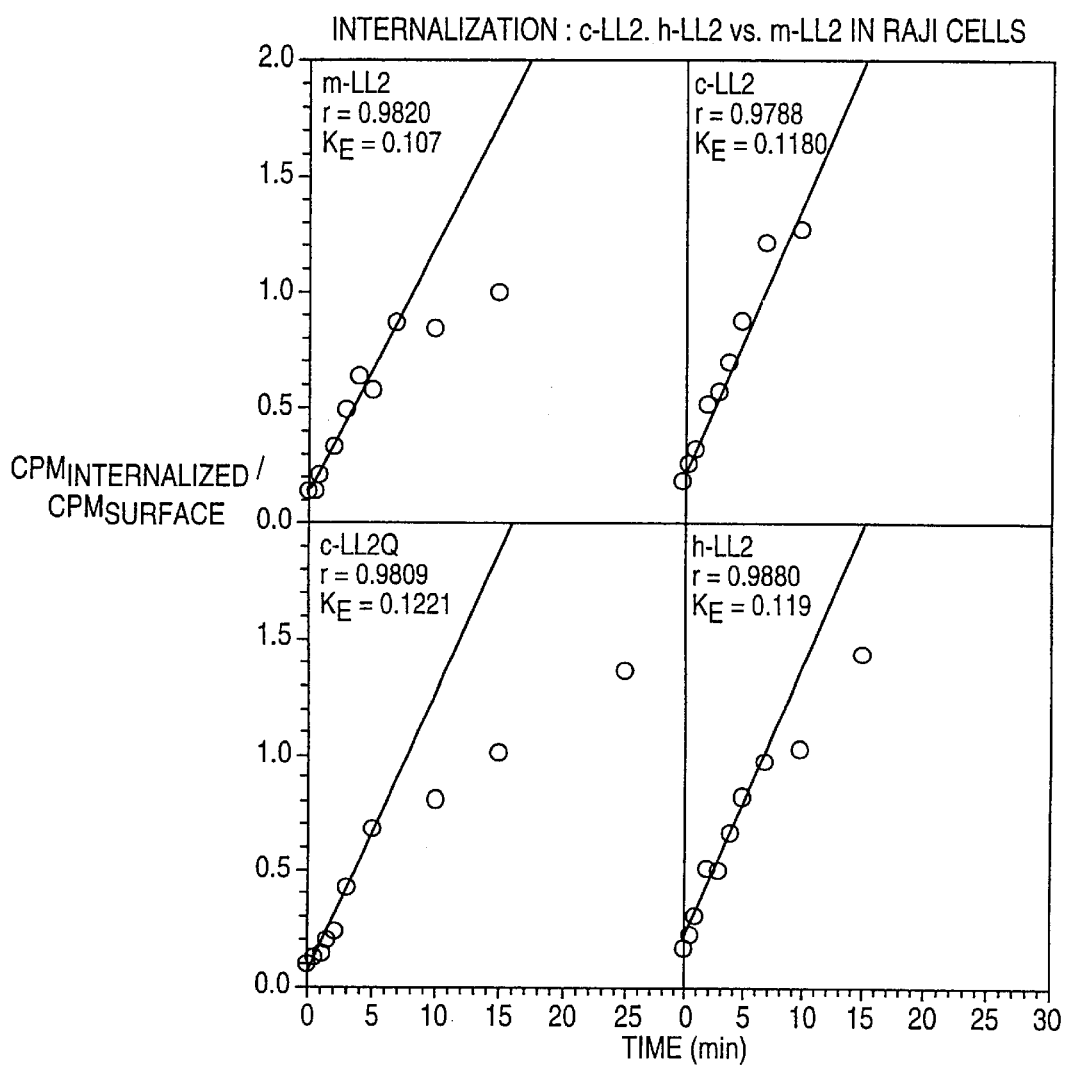
FIG. 9 shows a comparison of antibody internalization-:surface binding ratios as a function of time for cLL2, cLL2 (Q to V mutagenesis), hLL2 and mLL2 antibodies.

As shown in FIG. 9, mLL2, cLL2, cLL2Q and hLL2 antibodies were internalized at a similar rate (Ke=0.107 (mLL2) to 0.1221 (cLL2Q, NVT to QVT mutation). Those numbers suggested that approximately 50% of the surface-bound antibody could be internalized in 10 min. The results show that neither chimerization nor humanization nor deglycosylation by mutagenesis of mLL2 antibodies impair rates of internalization.

The pattern of internalization for mLL2, cLL2 and hLL2 was also monitored by fluorescence microscopy on a time-course basis using a FITC-labeled second antibody probe as described in the specification. Internalization of both antibodies was observed in at the earliest time point measurable. At 5 minutes, antibodies were seen both on the cell surface and internalized in areas immediately adjacent to the membrane as cytoplasmic micro-vesicles. At 15 min. post-incubation, the fine dots dispersed around the intramembrane began to merge into a group of granules, at locations believed to be the Golgi apparatus. As more antibodies were being internalized after 30 min. of incubation, redistribution of the grouped antibodies to scattered locations, probably the lysosome in which the antibodies were degraded, was observed. At 2 hrs post-incubation, most of the antibodies were found inside the cell. only strong surface staining was observed when LL2 was incubated for 20 min on ice. Both mLL2 and cLL2 were internalized with a similar pattern. The internalization of LL2 was associated specifically with antigen-antibody binding, as the irrelevant control humanized antibody demonstrated only dull surface staining.

The A103 antibody (an IgG2a antibody that binds to the surface of all human epithelial cells but does not internalize efficiently (Mattes et al., *Hybridoma*, 2: 253 (1983)) showed strong membrane staining at up to 2 h, while the anti-transferrin receptor antibody (5F9) internalized rapidly, just as did LL2.

EXAMPLE 8

Role of Glycosylation Site in FR1 Region of LL2 VK Sequence

Of particular inventive interest is the identification of an Asn-glycosylation site at position 18–20 within the FR1 region of the LL2 NVT light chain sequence (FIG. 4A, SEQ ID NOS:1 & 2). As shown above, SDS-PAGE analysis under reducing condition suggests that the Asn glycosylation site is utilized for carbohydrate addition. In this example, the influence of the carbohydrate moiety at position 18–20 on the functional activities of the light chains was examined.

Murine and chimeric LL2 light chains, treated or untreated with endoglycosidases F, were examined by SDS-PAGE under reducing and non-reducing conditions. There was no distinction between the antibody types as to electrophoretic behavior. In both cases, deglycosylation reduced the rate of migration of the light chain.

Figure 10:
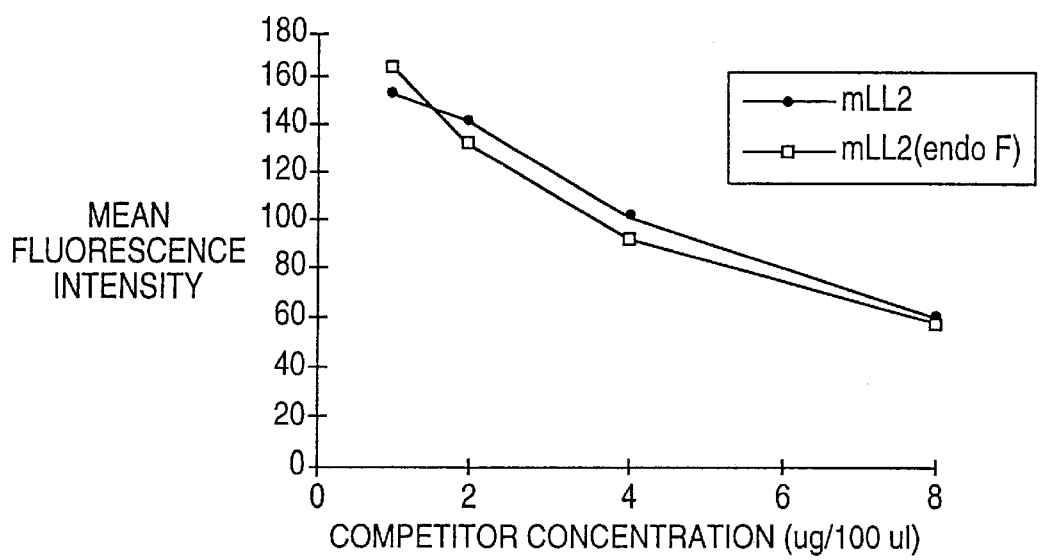
FIG. 10 shows the effect of deglycosylation of mLL2 on its binding affinity to Raji cells.

The effect of deglycosylation on the binding affinity to Raji cells of the mLL2 antibody is shown in FIG. 10. Removing carbohydrate by endoglycosidases F did not influence the binding activity.

A mutation was introduced at position 18 of the light chain so that the Asn was replaced with Gln to produce LL2Q VK FR1. SDS-PAGE analyses demonstrated that the NVT to QVT mutation abolished glycosylation of the antibody. Comparison of the Raji cell binding affinity for cLL2 with and without light chain VK glycosylation demonstrated that the carbohydrate moiety did not influence binding of the antibody to these cells.

It can be concluded that the presence of the carbohydrate site in the variable region does not affect the immunoreactivity of the antibody. Computer modeling studies suggested that the VK carbohydrate moiety in LL2 is remotely positioned from the CDRs and forms a "cap" over the bottom loops of the FR-associated β-barrels supporting the CDRs. Humanization without inclusion of the original glycosylation site resulted in a CDR-grafted LL2 antibody with immunoreactivity comparable to that of its murine counterpart. These characteristics indicate that the glycosylation site can be used for conjugating therapeutic or diagnostic agents to LL2 without compromising the ability of the antibody to bind and internalize in B-lymphoma or leukemia cells.

EXAMPLE 9

Conjugation of LL2 at its VK Region Carbohydrate-bearing Site

The apparent lack of involvement of the variable region carbohydrate moiety in the functional activities of mLL2, cLL2 and hLL2 mabs indicates that this moiety could profitably be used as the site of attachment of cytotoxic or detection agents such as radionuclides or toxins, and thereby avoid potential interference with the binding of the conjugate to a cell surface.

Using procedures described in Shih et al., U.S. Pat. No. 5,057,313 (which is incorporated by reference) for preparing antibody conjugates through an oxidized carbohydrate moiety of the antibody and a primary alkylamine group of a polymeric carrier to which are covalently one or more of a variety of drugs, toxins, chelator and detectable labels, a doxorubicin-dextran-LL2 antibody fragment devoid of appended glycan was produced containing multiple copies of the drug. The carbohydrate moieties of the cLL2 VK FR1 region involved were those covalently bound to the Asn glycosylation site.

In one synthesis, dextran (18–40 kDa) was converted to an amino dextran by oxidation of the dextran by $NaIO_4$, Schiff base formation with $NH_2$—$CH_2$—$CHOH$—$CH_2$—$NH_2$, and reduction with $NaBH_4$. The amino dextran was then condensed with doxorubicin (DOX) in the presence of succinic anhydride and 1-ethyl-3-(3-dimethylaminopropyl) carbodiimide to produce DOX-aminodextran. The latter was then condensed with an aldehydic group on LL2 VK FR-1 produced by oxidizing the carbohydrate moiety of the antibody fragment with $NaIO_4$.

In one preparation of DOX-LL2, the number of moles of DOX attached to dextran was 14 moles per mole dextran, and the number of moles of doxorubicin per mole F(ab')2 was 8.9. The immunoreactivity in the Raji cell binding assay above was about 80% of control values. This conjugation system is not limited to the mLL2 antibody. In a comparative study, 15–19 moles of DOX were bound per mole of cLL2.

The conjugation possibilities are not limited to the use of a carrier dextran as in the example above. For example, the carbohydrate moiety of the LL2 VK FR1 region can be oxidized to produce aldehydic groups. These in turn can be reacted with an amino group on any drug to produce a Schiff base which, upon reduction, produces multiple copies of the drug stably linked to the antibody via alkylamine groups.

For example, where the drug is aminohexyl DTPA (a chelating agent), there is produced a LL2 covalently bound to a chelator. The chelator can be used to deliver to target tissues, for example, a radionuclide or paramagnetic metal ion, with a potential for diagnostic and therapeutic uses. DTPA-LL2 conjugates were produced containing 5.5 moles of the chelator/mole of antibody which, in turn, chelated 47.3% of Y-90 and 97.4% In-111

EXAMPLE 10

Enhanced Production of a Humanized Anti-B-cell Lymphoma Antibody

Despite a demonstrated efficacy for murine LL2 in the treatment and diagnosis of non-Hodgkin's B-cell lymphoma, a thorough study of the clinical significance of its humanized version (hLL2), however, was rendered difficult due to the low hLL2 productivity of the original transfectoma (ca. 1 mg/liter in a terminal culture). By re-ligating the hLL2 heavy and light chain sequences into an expression vector containing an amplifiable dihydrofolate reductase gene (dhfr) (hLL2pdHL2), we were able to transfect the vector into SP2/0 cells by electroporation and generate a methotrexate (MTX) resistant and hLL2 producing clone. At a MTX concentration of 0.1 $\mu$M, 1.4 mg of hLL2 were purified from a one-liter terminal culture. The level of hLL2 production rose with stepwise increases in the concentration of MTX in the culture media, and reached a production plateau of 70+/−5 mg/liter at 3 $\mu$M of MTX. The hLL2 thus purified exhibited a PI of 10.3 with conserved immunoreactivity. Furthermore, complete removal of MTX selection, and freezing and thawing did not appear to affect the high level productivity of the established clone, suggesting that the amplified genes were stably integrated into the chromosome.

EXAMPLE 11

Construction of N-linked Glycosylation Sites into the ConstantRregion of hLL2 Antibody 1. Designing N-linked glycosylation site mutations.

(1) Light chain mutations.

Potential N-linked glycosylation sequences have been identified in the kappa constant regions of rabbit antibodies at a.a. position 161–163 and 174–176. Similar sites can be introduced into the CK domain of hLL2, designated as sites KCNI and KCN2, respectively. Additionally, three other CK mutants, namely KCN3, KCN4 and KCN5 were designed, as listed in FIG. 12.

(2) Heavy chain mutations.

Human IgM contains potential carbohydrate-addition-sequence, NNS, in the CH1 domain at amino acid position 161–163. Similarly, the sequence, NVT, was positioned at the residues 168–170 in the $CH_1$ domain of human IgA. By the same rationale used in the designs of light chain mutations, certain heavy chain mutations also were introduced (FIG. 12).

Carbohydrate-addition-sequence, Asn-Asn-Ser, was identified at a.a. positions 161–163 (Kabat's numbering; Kabat et al., 1991) in some of the human IgN CH1 domains. Similarly, the sequence, Asn-Val-Thr, was positioned in a.a. positions 168–170 in the CH1 domain of human IgA. By mutating the human IgG1 sequence Asn-Ser-Gly to Asn-Ser-Val at a.a. positions 162–164, Ala-Leu-Thr to Asn-Leu-Thr at a.a. positions 165–167, and Leu-Thr-Ser to Asn-Thr-Ser at a.a. positions 166–168, respectively, three potential N-linked glycosylation sites, most analogous to that of IgM and IgA, were introduced into the CH1 domain of human IgG1, with minimal interference on the resultant structure. Such glycosylation sites may thus remain in a "natural" position. Other glycosylation acceptor sequences were introduced based on their surface accesibility as predicated by computer modeling (HCM5, for example). Yet other sites were chosen randomly, by facility to mutate the sequence, without modeling.

2. Engineering mutation constructs for expression.

(1) Design and synthesis of primers for mutagenesis.

Oligonucleotide-directed site specific mutagenesis was used to introduce the designed potential N-linked glycosylation sites in hLL2 antibody. The oligonucleotide primers corresponding to each CK and CHI mutation were synthesized and used for in vitro mutagenesis. Each of these primers also introduced into the target DNA fragment a restriction cleavage site (Table 1, underlined sequences) to facilitate subsequent screening process. In Table 1, the bold letters indicate the mutated bases.

TABLE 1

```
CK mutation primers:

CKN1 (SEQ ID NO:34) 5'-CCAATCGGGTAATTCGAATGAGAGTGTCACAGAG-3'

CKN2 (SEQ ID NO:35) 5'-GGACAGCACCTACAACTTAAGCAGCACCCTGAC-3'

CKN3 (SEQ ID NO:36) 5'-GGAAGGTGGATAACGCGTCCCAATCGGGTAA-3'

CKN4 (SEQ ID NO:37) 5'-AGCAGCACCCTAAATTTGAGCAAAGCAGACT-3'

CKN5 (SEQ ID NO:38) 5'-GAGTGTCACAGAGAACGTTAGCAAGGACAGCACC-3'
CH₁ mutation primers:

HCN1 (SEQ ID NO:39) 5'-GTGTCGTGGAACTCAAGCGCTCTGACCAGCGGC-3'

HCN2 (SEQ ID NO:40) 5'-TTCCCGGCTGTCCTGAATTCCTCAGGACTCTACT-3'

HCN3 (SEQ ID NO:41) 5'-CCTCAGGACTCTACTCGAATTCCAGCGTGGTGACCGT-3'

HCN4 (SEQ ID NO:42) 5'-GTGGTGACCGTCCCGAATTCCAGCTTGGGCACC-3'

HCN5 (SEQ ID NO:43) 5'-GCCCTCCAGCAGCAACGGTACCCAGACCTACATCTGC-3'
```

(2) Construction of expression vectors.

By in vitro site-specific mutagenesis, potential N-linked glycosylation sequences were introduced into the genes encoding the light and heavy chain of hLL2. The sequences were confirmed by DNA sequencing. Each mutated gene was then subcloned into the corresponding expression vector (hLL2pKh for the kappa chain and hLL2pG1g for the heavy chain).

The CH1 domain of human IgGI was first excised from the expression vector LL2pG1g containing the human genomic IgG1 constant region sequence (Leung et al., 1994b) by digestion with the restriction enzymes BamHI and BstXI, and subcloned into the corresponding sites of the pBluescript SK vector (Stratagene, La Jolla, Calif.) for further manipulations. The resultant vector is designated as CH1pBS.

Mutations were accomplished using the Transformer™ Site-Directed Mutagenesis Kit (CLONTECH, Palo Alto, Calif.) according to the manufacturer's specifications. The selection primer, MutKS (SEQ ID NO:44) (5'-ACG GTA TCG ATA TGC ATG ATA TCG AAT T-3'), is designed for use in conjunction with the respective mutation primers in all cases. It was chosen to convert the HindIII restriction site in the cloning sequence of pBluescript to a NsiI restriction site (underlined).

To mutate Asn-Ser-Gly to Asn-Ser-Thr at a.a. positions 162–164, the selection primer MutKS and the primer CHO162 (SEQ ID NO:45) (5'-GTG TCG TGG AAT TCA ACC GCC CTG ACC AGC GGC-3') were used to change the Gly at position 164 will be mutated to Thr. An EcoRI site (underlined) is also included in the mutagenic primer as a diagnostic site.

To mutate Ala-Leu-Thr to Asn-Leu-Thr at a.a. positions 165–167, the selection primer MutKS and the mutation primer CHO165 (SEQ ID NO:45) (5'-GTG TCG TG G AAT TCA GGC AAC CTG ACC AGC GGC-3') are used to change the Ala-165 to Asn-165. An EcoRI site (underlined) is included in the mutagenic primer as a diagnostic site.

To mutate Leu-Thr-Ser to Asn-Thr-Ser at a.a. position 166–168, the selection primer MutKS and the mutation primer CHO166 (SEQ ID NO:47) (5'-TGG AAC TCA GGC GCG AAT ACC AGC GGC GTG CAC-3') were used to change the Leu-166 to Asn-166. The KasI site (GGC GCC) in the original CH1 sequence of human IgG1 is deliberately eliminated by changing the 3' C into a G for diagnostic purposes.

The phosphorylated primer pairs (selection and the respective mutation primers) at 100 ng each are annealed to 100 ng of the staging vector, CH1pBS, in 20 mM Tris-CH1 (pH 7.5), 10 MM MgCl₂, 50 mM NaCl in a final volume of 20 μl by incubation at 95° C. for 3 min, and then chilling on ice for 5 min. To the mixture, 2 to 4 units of T4 DNA polymerase, 4 to 6 units of T4 DNA ligase together with 3 l of 10× synthesis buffer (CLONTECH, Palo Alto, Calif.) are added. After an incubation period of 2 hr at 37° C., the polymerization and ligation reactions are terminated by heating at 65° C. for 5 min in the presence of 3 l of prewarmed stop solution (0.25% SDS, 5 mM EDTA). DNA from the mixture is used to transform electrocompetent E. coli cells, BNH71-18 mutS (repair deficient), by the method of electroporation. Transformants are then pooled and grown overnight in SOC (20 mg/ml bacto-tryptone, 5 mg/ml bacto-yeast extract, 8.6 mM NaCl, 2.5 mM KCl, 20 mM glucose) with 50 g/ml ampicillin at 37° C. Mini-plasmid DNA preparations from the pooled transformants are digested with HindIII to linearize DNA not mutated with the selection primer. After the enzymes are removed by phenol extraction, the DNA is used for a second transformation with competent DH5 cells. Plasmid DNA that fails to be digested with HindIII is examined for the presence of the EcoRI diagnostic site (in the case of Gly to Thr, and Ala to Asn mutations), or the absence of the KasI diagnostic site (in the case of the Leu to Asn mutation). Final confirmation of the mutation is accomplished by Sanger's dideoxy sequencing (Sanger et al., 1977). The CH1 region confirmed to have the desired mutations is then excised with BamHI/BstXI enzymes and cloned into the corresponding site of the final heavy chain expression vectors for hLL2, hLL2pG1g.

(3) Expression vector for gene amplification.

In order to facilitate down stream process of antibody production, it is desirable to utilize a gene amplification system for antibody expression. After an antibody variant is proved to have industrial potential, high level production could be achieved by gene amplification. From this consideration, we planned to construct these N-linked glycosylation site mutants in the hLL2pdHL2 high level expression vector, a dhfr mini gene based amplification system. Heavy chain mutations, HCN3, HCN4, and HCN5, were subcloned into this vector for expression.

The final expression constructs for these mutations were designated as hLL2HCN3pdHL2, hLL2HCN4 and hLL2HCN5pdHL2, respectively.

3. Expression of mutant hLL2 and glycosylation at engineered sites. The constant domains containing the engineered glycosylation sites were ligated to the respective variable (V) regions of hLL2. The different glycosylation mutants were expressed in murine SP2/0 myeloma cells which were transfected with the heavy and light chain expression vectors by electroporation. The engineered antibodies were purified from the culture supernatant of the stable antibody-producing cells by protein A columns, and the purified proteins analyzed on SDS-PAGE under reducing conditions. The heavy chains of the glycosylation mutants migrated at different rates compared to that of the control antibody, hLL2, whose CH1 domain did not contain any potential glycosylation sites. Since the SDS-PAGE migration rate is inversely proportional to the molecular sizes of the engineered oligosaccharides, the extent of glycosylation at the different sites should be in the order of HCN5>HCN1>HCN3>HCN2>HCN4 with hLL2HCN5 and hLL2HCN1 being the two most highly glycosylated Ab. By contrast, judging from the lack of migration retardation in the light chains for the mutants KCN1–4 we concluded that these CK-associated sites were either not glycosylated at all, or glycosylated at an insignificant level.

4. hLL2HCN1 and hLL2HCN5 are N-glycosylated in the $CH_1$, domain. The antibodies hLLHCN1, hLL2HCN5 and hLL2 were treated with N-glycosidase F (PNGase F), which specifically cleaves all types of Asn-bound glycan from peptides, and were analyzed on reducing SDS-PAGE. The higher apparent molecular masses for the heavy chains of hLL2HCN1 and hLL2HCN5 were reduced to that of hLL2 after PNGase F digestion indicating that the size difference between these Abs were attributed to the heavy chain associated N-linked CHOs. It should be noted that, all human $IgG_1$, Abs are naturally glycosylated in the $CH_2$ domain at Asn297. The size differences observed might be due to differential glycosylation at the CH2 site, rather than at the engineered sites, as a result of variations in the culture condition. We therefore prepared F(ab')2 fragments of hLL2HCN1, hLL2HCN5 and hLL2, and analyzed these fragments on reducing SDS-PAGE. The size differences between the Abs were shown to be associated with the Fd fragments (VH–$CH_1$), which are devoid of the Fc portion and the appended oligosaccharides, the molecular size for Fd fragments of hLL2HCN5 being larger than that of hLL2HCN1. When fragments were deglycosylated by PNGcase F treatment, these size differences were eliminated and all Fd fragments migrated at the same position as the unglycosylated hLL2, suggesting that the engineered sites were actually used for glycosylation and the extent of glycosylation for HCN5 site was larger than that of HCN1.

The N-linked oligosaccharide moieties in the $CH_1$, domain of hLL2HCN1 were directly visualized by CHO-specific labeling. The oligosaccharide moieties attached to the were first periodate oxidized. The aldehydes groups generated were then covalently conjugated with biotin, which was probed and visualized by streptavidin-peroxidase in a western blotting analysis. As we anticipated, only the heavy chain but not light chains of both hLL2 and hLL2HCN1 were visible with CHO labeling. When quantified with densitometry, the intensity of labeled CHOs in hLL2HCN1 was approximately 2.5-fold of that in hLL2. The protein contents of the different Abs analyzed were comparable, as shown by coomassie blue-stained SDS-PAGE. We attributed this difference in intensity to be the result of additional glycosylation in the engineered HCN1 site. This was confirmed when the F(ab')$_2$ fragments were subjected to the same analysis: only the Fd fragment of hLL2HCN1 but not that of hLL2 demonstrated CHO specific labeling. By contrast, potential CK glycosylation sites were not found to be glycosylated.

It should be noted that, unlike the VK-appended glycosylation site which exhibited heterogeneity in the degree of glycosylation, only one discrete band was observed in the SDS-PAGE analysis for hLL2 (HCN1) Fd fragment. It is speculated that almost all of the Fd fragments of hLL2 (HCN1) were glycosylated, and the degree of glycosylation was relatively homogenous, a desirable property that would facilitate their subsequent characterizations and applications.

5. WN competitive binding assay.

Figure 11:
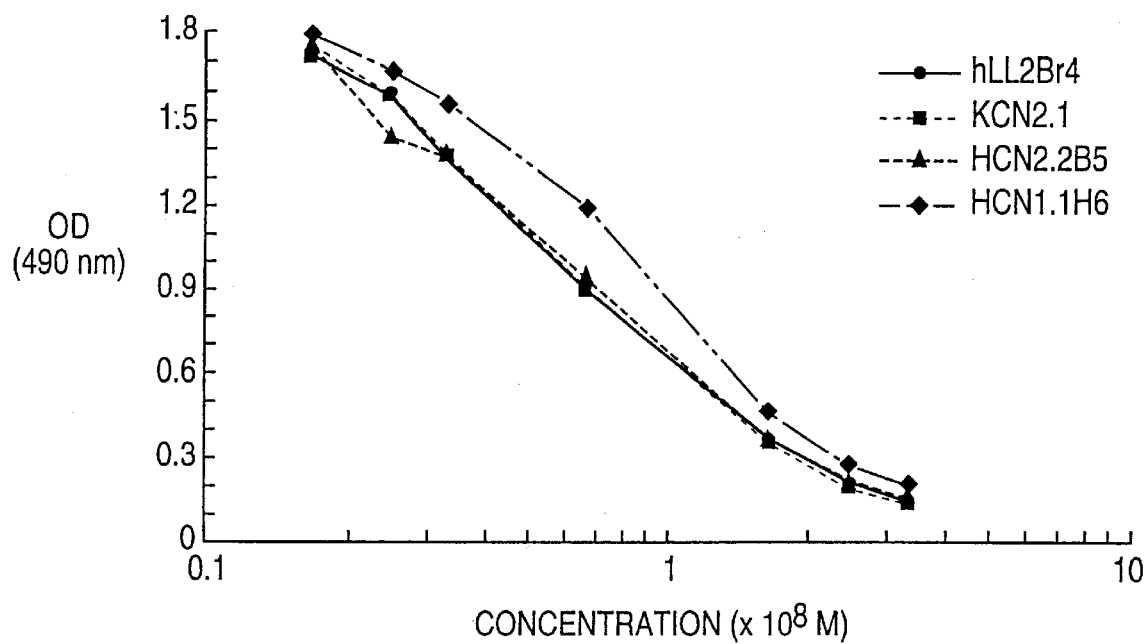
FIG. 11 shows a competitive binding assay where peroxidase conjugated mLL2 binding to WN was measured. hLL2 and glycosylated derivatives in the heavy chain constant regions, at the indicated concentrations, were used to compete with mLL2.

The antigen-binding property of these two antibodies was evaluated by competition binding with mLL2 to an LL2 anti-idiotype antibody (WN). This assay showed that the binding activity of hLL2HCN1 and hLL2HCN2 to WN is indistinguishable from that of hLL2. (FIG. 11).

EXAMPLE 12

Site-specific Conjugation of Aminobenzyl DTPA and Dextran-doxorubicin to hLL2HCN1 and hLL2HCN5

The site-specific modification of the F(ab')$_2$ fragments of antibodies with DTPA was as described. See Leung et al., *J. Immunol.* 154:5919 (1995). F(ab')$_2$ fragment (~1 mg/ml) was oxidized with 15 mM of sodium metaperiodate at 4° C. for 1 h. The oxidized material was purified, mixed with 545-fold molar excess of aminobenzyl DTPA and the pH was adjusted to 5.97. The mixture was incubated in the dark at ambient temperature for 5 h, and then kept at 4° C. for 18 h. The conjugates were stabilized with 10 mM of sodium cyanoborohydride, purified and concentrated. The chelator:F(ab')$_2$ ratio was determined by metal binding assays and use of indium acetate spiked with $^{111}$In. See Meares et al., *Anal. Biochem.* 142:68 (1984). Radiolabeling was performed as described. See Leung et al., (1995), supra. The number of DTPA molecules conjugated to F(ab')$_2$ fragment was determined by metal-binding assay using In/In-111 system. Briefly, 40 μg of the conjugates was incubated for 30 min with a known excess of indium acetate, spiked with In-111 acetate. The solution was made 10 mM in EDTA, and incubated for further 10 min. The labeling was analyzed by ITLC using 10 mM EDTA for development. DOX-dextran conjugate was prepared as described by Shih et al., *Cancer Res.* 51: 4192 (1991), using amino-dextran of 18 kDa as the intermediate carrier. The intermediate conjugate possessed a substitution level of 10.5 DOX molecules per dextran polymer. DOX-dextran was then conjugated with the F(ab')$_2$ fragment of hLL2HCN1 or hLL2HCN5. Briefly, the antibody fragment was concentrated to 10 mg/ml in 0.1 M sodium acetate buffer, pH 5.5, and treated with 20 mM of sodium metaperiodate in the dark at 4° C. for 60 min. The oxidized antibody was purified on a Bio-Spin column (Bio-Rad) that was pre-equilibrated in 0.05 M HEPES buffer, pH 8.0, containing 0.1 M NaCl, and then treated with DOX-dextran (4 equivalents) at room temperature for 24 h. After sodium borohydride reduction, the conjugated product was purified on a Bio-gel A-0.5m gel column (Bio-Rad). The protein fractions were pooled and concentrated in Centricon 50 concentrator (Amicon, Beverly, Mass.). The trace amount of intermediates in the protein conjugates was removed by repetitive washing with the conjugation buffer as evaluated by HPLC on Bio-Sil Sec size exclusion column (Bio-Rad).

EXAMPLE 13

$CH_1$-appended Oligosaccharides can be used as Efficient Conjugation Sites for Chelates and/or Drugs.

Under mild chemical conditions, an average of 1.6 and 2.97 molecules of DTPA were conjugated onto each F(ab')2 fragment of hLL2HCN1 and hLL2HCN5, respectively (Table 2). Both conjugates demonstrated high efficiencies in $^{111}$In incorporation (92% for hLL2HCN1, 91% for hLL2HCN5). No significant changes in immunoreactivities were observed before and after DTPA conjugation of the glycosylation mutant fragments, as evaluated in a WN competitive blocking assay. HCN5-appended CHO appeared to be more reactive for chelate conjugation when compared to the HCN1-appended CHO; almost twice as many DTPA molecules could be incorporated into the HCN5 site.

Leung et al. (1995), supra, has shown that the VK-appended CHO found in murine LL2 can be used as a site-specific conjugation site for small chelates without reducing the Ag binding property of the Ab. The effect of conjugating this VK-appended CHO with dextran-DOX complex on immunoreactivity was examined. The dextran-DOX complex was generated by chemically incorporating an average of 10 DOX molecules onto an 18 kDa amino-dextran polymer. Using the amino-dextran as the carrier for DOX, approximately 5.1 DOX molecules on average were incorporated onto the VK-appended CHO of murine LL2, and a reduction of close to 60% of immunoreactivity as evaluated by cell binding and ELISA assays, was observed. See Table 3. Conjugation of slightly higher number of DOX molecules (6.8) onto the HCN1 CHO, however, was comparatively less detrimental in term of its effect on immunoreactivity; only 30% reduction in the resultant binding affinity was noted. In contrast, no significant changes in Ag binding property (less than 5% reduction) were apparent when similar number of DOX molecules (7.2) was conjugated at the HCN5 CHO. See Table 3.

The molecular masses of the F(ab')$_2$ fragments of hLL2, hLL2HCN1 and hLL2HCN5 determined by mass spectrometry analysis (Mass Consortium, San Diego, Calif.) were 99,000, 102,400 and 103,800, respectively since these fragments are identical in sequences, except at the engineered site (one amino acid difference), and the fragments did not carry the glycosylated Fc portion, the molecular mass difference between the F(ab')2 of hLL2 and the glycosylation mutant should represent the molecular weights of the different CH1-appended CHOS, i.e., 3.4 and 4.8 kD for the CHOs at the HCN1 and the HCN5 sites, respectively.

By PNGase F digestion, the CH1-appended CHOs of hLL2HCN1 and hLL2HCN5 were released for profiling and sequencing analyses using fluoropore-assisted carbohydrate electrophoresis (FACE). Heterogenous populations of CH1-appended CHO species were identified. About 60% of the oligosaccharides from HCN5 site were of the larger tri-antennary structure, while that from HCN1 were mainly bi-antennary (>90%). These results are consistent with the mass spectrometry studies indicating a larger average molecular size of the CHO at the HCN5 sites compared to that of HCN1.

It should be emphasized that the above-described examples merely describe several specific embodiments of the invention, and applicants do not intend to be limited as to scope of claims by these specific examples.

Applicants also incorporate by reference all publications and patents cited in the specification.

TABLE 2

Site-specific conjugation of DTPA and radiolabeling.

| Antibody | Efficiency[a] | | $^{111}$In labeling | | Immunoreactivity | |
|---|---|---|---|---|---|---|
| (%) F(ab')$_2$ | DTPA | DTPA// F(ab')$_2$ | % Incorp.[b] | μCi/ μg[c] | ID$_{50}$ | % of hLL2[d] |
| hLL2 | Non-conj. | NA | NA | NA | 0.384 (±0.021) | 100 |
| hLL2HCN1 | Non-conj. | NA | NA | NA | 0.355 (±0.038) | 100 |
|  | Conjugated | 1.6 | 92 | 6 | 0.387 (±0.042) | 100.8 |
| hLL2HCN5 | Non-conj. | NA | NA | NA | 0.443 (±0.039) | 115.4 |
|  | Conjugated | 2.97 | 91 | 5.6 | 0.356 (±0.077) | 92.7 |

[a]A control experiment using hMN14 F(ab')$_2$ (non-glycosylated) yield a negligible chelate/F(ab')$_2$ ratio of 0.075, confirming that conjugation were indeed directed to the carbohydrate moieties.
[b]Determined by cobalt/cobalt-57 or indium/indium-111 assays (Meares et al., Anal. Biochem. 142:68, 1984).
[c]HPLC yields; percentage of labeling in each case was higher by using ITLC analysis; colloidal metal was less than 1% in all labeling.
[d]On the basis of comparisons to the ID$_{50}$ of unmodified control F(ab')$_2$ in competitive binding assays.
ND: not determined

TABLE 3

Site-specific conjugation of doxorubicin.

| Antibody | Efficiency[b] | | Immunoreactivity (%) | |
|---|---|---|---|---|
| F(ab')$_2$ ELISA[d] | Dextran-DOX | Yield[a] (%) | (DOX/ F(ab')$_2$ | Cell binding[c] |
| mLL2 | Non-conj. | NA | NA | 100 | 100 |
|  | Conjugated | 55 | 5.1 | 41.9 | 42.2 |
| hLL2HCN1 | Non-conj. | NA | NA | 100 | 100 |
|  | Conjugated | 30 | 6.8 | 70 | 70.6 |
| hLL2HCN5 | Non-conj. | NA | NA | ND | 100 |
|  | Conjugated | 80 | 7.2 | ND | 94.8 |

[a]Determined by spectrophotometry.
[b]Determined and calculated by spectrophotometry.
[c]Activity determined by a cell surface binding assay as described in and calculated from the ID50 values.
[d]Immunoreactivity Calculated from the ID50 values.

What is claimed is:

1. A monoclonal antibody or antigen-binding fragment thereof which is engineered to contain a glycosylation site in the non-Fc constant heavy chain region.

2. The monoclonal antibody or fragment of claim 1, which is a humanized antibody or fragment.

3. The monoclonal antibody or fragment of claim 2, which is a humanized B-cell specific antibody or fragment.

4. The monoclonal antibody or fragment of claim 3, wherein said glycosylation site is located on a site in the sequences selected from the group consisting of the HCN1, HCN2, HCN3, HCN4, and HCN5 sites (SEQ ID NOS:10–14) of FIG. 12.

5. The monoclonal antibody or fragment of claim 4, wherein said glycosylation site is located in the HCN5 site (SEQ ID NO:14) of FIG. 12.

6. The monoclonal antibody or fragment of claim 4, wherein said glycosylation site is located in the HCN1 site (SEQ ID NO:10) of FIG. 12.

7. The monoclonal antibody or fragment of claim 3, wherein the antibody which is engineered to contain a glycosylation site is an antibody having the binding specificity of the hLL2 antibody.

8. An isolated DNA molecule comprising a gene encoding an antibody heavy chain which comprises a sequence within the CH1 region that, when said gene is coexpressed in a cell that is capable of glycosylation with a second gene encoding an antibody light chain will produce an antibody glycosylated in the CH1 region.

9. A method of producing an antibody or antibody fragment glycosylated in the CH1 region, comprising coexpressing light and heavy chain genes operably linked to expression control elements, wherein said genes have been engineered with a mutation such that a glycosylation site is created in the CH1 region of said heavy chain gene, in a cell that allows glycosylation, such that said antibody or antibody fragment glycosylated in the CH1 region is produced, and isolating said antibody or antibody fragment.

10. In a method of diagnosis or treatment of a patient wherein a monoclonal antibody or antibody fragment is administered to said patient to target a specific antigen, the antibody or fragment being used as such or conjugated to a diagnostic or therapeutic agent, the improvement wherein said antibody or fragment is the humanized monoclonal antibody or antibody fragment of claim 2.

11. The method of claim 10, wherein said patient suffers from a B-cell malignancy and said humanized monoclonal antibody or antibody fragment is a B-cell specific antibody or antibody fragment.

12. The method of claim 10, where said diagnostic or therapeutic agent is conjugated to a carbohydrate of said monoclonal antibody or antibody fragment.

* * * * *